US009485345B2

(12) United States Patent
Dantu et al.

(10) Patent No.: US 9,485,345 B2
(45) Date of Patent: Nov. 1, 2016

(54) 911 SERVICES AND VITAL SIGN MEASUREMENT UTILIZING MOBILE PHONE SENSORS AND APPLICATIONS

(71) Applicant: University of North Texas, Denton, TX (US)

(72) Inventors: Ramanamurthy Dantu, Richardson, TX (US); Vikram Chandrasekaran, Levittown, PA (US); Neeraj K. Gupta, Allen, TX (US)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 340 days.

(21) Appl. No.: 13/623,273

(22) Filed: Sep. 20, 2012

(65) Prior Publication Data

US 2013/0072145 A1   Mar. 21, 2013

Related U.S. Application Data

(60) Provisional application No. 61/537,382, filed on Sep. 21, 2011.

(51) Int. Cl.
 *H04M 3/42* (2006.01)
 *H04M 1/725* (2006.01)
 (Continued)

(52) U.S. Cl.
 CPC ........ *H04M 1/72536* (2013.01); *A61B 5/0022* (2013.01); *A61B 5/02416* (2013.01); *A61B 5/0816* (2013.01); *A61B 5/113* (2013.01); *A61B 5/6898* (2013.01); *G06F 19/3418* (2013.01); *H04M 11/04* (2013.01); *H04W 4/22* (2013.01); *A61B 5/02438* (2013.01); *A61B 7/003* (2013.01); *H04M 2250/52* (2013.01)

(58) Field of Classification Search
 CPC ........ A61B 5/00; A61B 5/02; A61B 5/0816; A61B 5/14551; A61B 5/0006; A61B 5/7232; A61B 5/7264; A61B 5/0022; A61B 5/021; A61B 5/6898; A61B 5/11; A61B 8/06; A61B 19/3431; A61B 17/30032; A61B 2220/807; A61B 5/02438; A61B 5/0205; A61B 5/024; G06F 19/3431; G06F 17/30032; G06F 19/3418; G06F 19/3481; H04W 76/007
 USPC ...................................... 455/404.1
 See application file for complete search history.

(56) References Cited

U.S. PATENT DOCUMENTS 5,544,661 A * 8/1996 Davis et al. .................. 600/513
2003/0036685 A1 * 2/2003 Goodman ..................... 600/300
(Continued)

OTHER PUBLICATIONS

Song, W., et al., "Next Generation 9-1-1 Proof-of-Concept System," SIGCOMM 2008.
(Continued)

*Primary Examiner* — Timothy Pham
(74) *Attorney, Agent, or Firm* — Jackson Walker LLP

(57) ABSTRACT

Improved methods for utilizing 911 services, for implementing 911 dispatch protocols, and for measuring vital signs of a human, all by accessing mobile phone sensors and applications, are disclosed. Vital signs such as heart rate, breathing rate, breathing distress, and blood pressure can be measured using mobile phone sensors and applications. A method for differential estimation of blood pressure involves the synchronization of time between two mobile phones, locating an appropriate position for one cell phone and recording heart sounds, and recording video data from the finger tip of the subject using the other mobile phone.

16 Claims, 21 Drawing Sheets

(51) Int. Cl.
*H04M 11/04* (2006.01)
*H04W 4/22* (2009.01)
*G06F 19/00* (2011.01)
*A61B 5/00* (2006.01)
*A61B 5/024* (2006.01)
*A61B 5/08* (2006.01)
*A61B 5/113* (2006.01)
*A61B 7/00* (2006.01)

(56) References Cited

U.S. PATENT DOCUMENTS

| | | | | |
|---|---|---|---|---|
| 2007/0189246 | A1* | 8/2007 | Molnar | 370/338 |
| 2007/0255115 | A1* | 11/2007 | Anglin et al. | 600/300 |
| 2008/0027337 | A1* | 1/2008 | Dugan et al. | 600/508 |
| 2008/0212746 | A1* | 9/2008 | Gupta et al. | 379/38 |
| 2009/0054799 | A1* | 2/2009 | Vrtis | G01N 33/497 600/532 |
| 2009/0203998 | A1* | 8/2009 | Klinghult et al. | 600/443 |
| 2011/0117878 | A1* | 5/2011 | Barash | G08B 21/0211 455/404.2 |
| 2011/0184295 | A1* | 7/2011 | Orbach et al. | 600/504 |
| 2012/0156933 | A1* | 6/2012 | Kreger et al. | 439/625 |

OTHER PUBLICATIONS

United Kingdom Department of Health—AMPDS Call Categorization Version 11; Her Majesty's Stationery Office, Apr. 2005.
SAMU Online (http://www.samu-de-france.fr/en).
NENA NG911 Project Online (http://www.nena.org/ng911-project).
NENA i3 Technical Requirements Document, (http://www.nena.org/standards/technical/voip/i3-requirements).
Nada Hashmi, Dan Myung, Mark Gaynor, Steve Moulton, "A Sensor-based web service-enabled emergency medical response system", EESR'05, Jun. 2005.
Fredrik Bergstrand, Jona Landgren, "Sharing Using Live Video in Emergency Response Work", Proceeding of the 6th International ISCRAM Conference—Gothenburg, Sweden, May 2009.
Roman Belda, Ismael de Fez, Francisco Fraile, Vicot Murcia, Pau Arce, Juan Carlos Guerri, "Multimedia System for emergency Services over TETRA-DVBT Networks", 34th Euromicro Conference Software Engineering and Advanced Applications, 2008.
Reinvuo T., Hannula M., Sorvoja H., Alasaarela E., Myllyla R., "Measurement of Respiratory Rate with High-Resolution Accelerometer and EMFit Pressure Sensor", IEEE Sensor Application Symposium, Feb. 2006.
Rendon D. B., Rojas Ojeda J.L. Crespo Foix L.F., Morillo D.S., Fernandez M. A., "Mapping the Human Body for Vibrations using an Accelerometer", Proceeding of the 29th Annual Conference of the IEEE EMBS, Aug. 2007.
Su S.W., Cellar B.G., Savkin A.V. Nguyen H.T., Cheng T.M., Guo Y., Wang L., "Transient and Steady State Estimation of Human Oxygen uptake based on Noninvasive Portable Sensor Measurements", Medical Biology Engineering Computation, Mar. 2009.
Phan D.H., Bonnet S., Guillemaud R., Castelli E., Pham Thi N.Y., "Estimation of Respiratory Waveform and Heart Rate using Accelerometer", 30th Annual International IEEE EMBS Conference, Aug. 2008.
Richard Chipman, Roger Wuerfel, "Network Based Information sharing Between Emergency Operations Center", IEEE Conference on Technologies for Homeland Security 2008.
Green M.W., Sparks R., Pritchard D.A., "Real-time Video Surveillance for First Responders in an Emergency Situation", IEEE International Conference on Security Technology 2008.
Jeong O., Lee I. Shin-Gak K., "Consideration of Supporting the Multimedia Emergency Services in VOIP", International Conference on Advanced Communication Technology 2009.
J. Alfie, G. D. Waisman, C. R. Galarza, and M. I. Camera, "Contribution of Stroke Volume to the Change in Pulse Pressure Pattern With Age," Hypertension, vol. 34, No. 4, pp. 808-812, 1999. [Online]. Available: http://hyper.ahajournals.org/cgi/content/abstract/34/4/808.
J. N. Cohn, S. Finkelstein, G. McVeigh, D. Morgan, L. LeMay, J. Robinson, and J. Mock, "Noninvasive Pulse Wave Analysis for the Early Detection of Vascular Disease," Hypertension, vol. 26, No. 3, pp. 503-508, 1995. [Online]. Available: http://hyper.ahajournals.org/cgi/ content/abstract/26/3/503.
K. Banitsas, P. Pelegris, T. Orbach, D. Cavouras, K. Sidiropoulos, and S. Kostopoulos, "A simple algorithm to monitor hr for real time treatment applications," Nov. 2009, pp. 1-5.
J. Y. A. Foo, C. S. Lim, and P. Wang, "Evaluation of blood pressure changes using vascular transit time," Physiological Measurement, vol. 27, No. 8, p. 685, 2006. [Online]. Available: http://stacks.iop.org/0967-3334/27/i=8/a=003.

* cited by examiner (a)

(b)

911 SERVICES AND VITAL SIGN MEASUREMENT UTILIZING MOBILE PHONE SENSORS AND APPLICATIONS

This application claims priority to U.S. Provisional Patent Application Ser. No. 61/537,382, entitled 911 SERVICES AND VITAL SIGN MEASUREMENT UTILIZING MOBILE PHONE SENSORS AND APPLICATIONS, filed on Sep. 21, 2011, the entire content of which is hereby incorporated by reference.

BACKGROUND

This disclosure pertains to improved methods for utilizing 911 services and for implementing 911 dispatch protocols by accessing mobile phone sensors and applications. This disclosure also pertains to measurement of vital signs of a patient using mobile phone sensors and applications, including estimation of blood pressure without a traditional stethoscope and cuff.

The United States 9-1-1 System has its origin in 1958, when the Commission on Law Enforcement and Administration of Justice suggested replacing the patchwork of local police and fire numbers with a single national emergency number. The dispatcher is an important player in the 911 call center. This is the person who takes information about the emergency and arranges adequate resources to be sent to handle the situation. The process of gathering information by the dispatchers to access the emergency situation has been standardized into documents called Dispatch Protocols. The first use of the standardized protocols was recorded in Arizona in 1975.

Table 1 below shows the data for various categories of calls received in percentage terms. The table shows that Medical emergencies account for the largest number of calls, followed by fire and vehicle accidents. The Other category has the largest number of calls, but includes calls that cannot be classified into any category. This number also includes calls that were considered non-emergency

TABLE 1

Category of 911 Calls

| Type of Emergency Call | Percentage of Total Calls |
|---|---|
| Medical Emergency | 37 |
| Fire | 11 |
| Vehicle/Accidents | 10 |
| Chemical Hazards | 2 |
| Floods/Water Damage | 1 |
| Electricity/Wire Down | 1 |
| Other | 38 |

Emergency dispatch protocols were based in legacy telecom networks where only voice calls were used and the networks were all based on dedicated landlines over a call connection. Over the years the technology has developed to include wireless networks in which the call connections are no longer dedicated landlines, but based on packet networks. The bandwidth of the networks has also increased to a point where multimedia services are available to the general public.

Emergency response services are provided in most of the advanced countries. The role of the emergency dispatcher has its origins in the United States, but it has gained acceptance in all parts of the world. In the US, the Dispatch Protocols are called the Medical Priority Dispatch System ("MDPS"). It is a system that has about 37 cards and each card gives instructions to the dispatcher for a specific emergency type. A similar Dispatch Protocol is used by the state of New Jersey and is called the Emergency Medical Dispatch Guidecards. This protocol also has a set of cards that the dispatcher uses based on the type of emergency call. These cards act as a guide to the dispatcher. The success of the notion of Dispatch Protocols can be gauged from the fact that today many developed countries have developed their own protocols. The UK uses AMPDS, while France uses its own version of Dispatch Protocols, called SAMU.

The 9-1-1 system in the U.S. has evoked to include, for example, wireless 9-1-1 services in 1998. In 205, the FCC mandated that Voice over IP ("VoIP") providers must offer 9-1-1 services also. Today, the architecture for Next Generation 9-1-1 ("NG911") has been designed by the National Emergency Number Association ("NENA"). NENA first identified the need for an overhaul of the 911 system in the year 2000. The first document describing the future path was produced in 2001 and by the end of 2003 the standards development activity had started. NENA is developing several documents relating to the architecture. Some of the documents are already complete. For example the overall requirements document is defined in NENA i3 Technical Requirements Document, available publicly.

Each year, about 200 million emergency calls are placed in the US, with about one third originating from mobile phones. With the deployment of NG911, there is the potential to better utilize the capabilities of these mobile phones to improve 911 services and dispatch protocols.

Measurement of vital signs in a human is an arduous task when sudden dizziness or fainting occur during unexpected situations. These occurrences are the most common symptoms of low blood pressure. Blood pressure, the amount of force applied on the walls of the arteries when the blood is forced throughout the body, depends on factors such as the amount of blood in the body, the pumping rate of the heart, the flexibility of the arterial walls, and the resistance to blood flow due to the size of the arteries. The blood pressure of a human varies continuously due to physical activity, medication, anxiety, and emotions. The body has unique mechanisms to regulate a person's blood flow; whenever a person's blood pressure drops, the heart rate increases to pump more blood and the arterial walls contract to increase the blood pressure. Blood pressure is given by two numbers measured in millimeters of mercury (mmHg). The first number is the systolic pressure, which represents the amount of pressure applied in the arteries when the heart contracts. The second number is the diastolic pressure, which represents pressure on the arteries when the heart is at rest.

Blood pressure is typically measured in the upper arm with the person comfortably seated and the arm in level with the heart. The measurement apparatus is a mercury sphygmomanometer comprising a manometer, pressure cuff, bladder and a gauge to show the pressure value inside the cuff which is wrapped tightly around the upper arm about an inch from the elbow since the upper arm is closest to the heart and therefore errors due to upflow/downflow of blood are eliminated. When this setup is done, the cuff is inflated to a pressure of about 210 mmHg or usually 20 to 30 mmHg above the normal systolic pressure. The gradual reduction of inflation causes a turbulent flow of blood, creating a sound. The cuff pressure corresponding to the first sound produced is taken as the systolic pressure. The cuff pressure is further reduced and when the sounds due to blood flow cannot be heard with the stethoscope. That cuff pressure is taken as the diastolic pressure.

However, to check a person's blood pressure during unexpected situations, there is a need for a portable, convenient device or apparatus. Despite the availability of digital wrist and arm blood-pressure meters, most people do not carry these devices during their daily commute to work place, gymnasiums, recreating facilities, or other places.

However, smartphones today have become increasingly popular with the general public for their diverse functionalities such as navigation, social networking, and multimedia facilities. These phones are equipped with high end processors, high resolution cameras, and built-in sensors such as accelerometer, orientation sensor and light-sensor. It is estimated that 25.3% of US adults use smart phones in their daily lives. Being prevalent in people's lives, it is highly desirable to utilize these mobile phones to measure vital signs of a human.

SUMMARY

The present disclosure relates generally to improved 911 services, emergency dispatch protocols, and vital sign measurement, including cuff-less differential estimation of blood pressure, utilizing mobile phone sensors and applications.

Today, most emergency calls are based on the Public Switched Telephone Network ("PSTN"). However, there were approximately 80 million Voice over IP ("VoIP") subscribers worldwide in 2007, and 50 percent of global telecommunications traffic is currently handled over IP networks. Although a small percentage of emergency calls are currently placed by VoIP subscribers, existing emergency calling systems must support IP-based emergency calls. To support IP-based emergency communications and the variety of new services that it allows, a new architecture is currently being developed and tested: Next Generation 9-1-1 (NG-9-1-1).

Telecom networks are moving toward Voice over IP protocols. Over time, an increasing number of calls will be made over these networks as opposed to the legacy networks. While these advances allow access to multimedia communications in everyday life, it also raises several issues that need to be resolved. Specifically for 911 calls, there are network related issues, such as identification of caller location (Song, W. et al. 2008). The challenges for these issues include:

Remote Media Control: Automatic remote control of cameras in the mobiles to change focus, lighting, contrast, Codecs, bandwidth, and such, to help prepare the call taker to better respond to the emergency.

Emergency Dispatch Protocols: Modification of Emergency Dispatch Protocols to take advantage of this new technology so as to reduce the number of questions asked over the phone and similarly reduce the number of instructions given.

High Availability: Quality of Service and traffic management need to be designed so that the 9-1-1 calls are not disrupted. This has always been true, but with multi-media services this issue also needs to be addressed.

Human Machine Interface (HMI): HMI is another very important research issue. The video screens at the call center will need a new design. There may be need for multiple screens or multiple windows on one screen. This includes requests, responses, and usability of screens on the operator side and also design of controls on the caller side.

Connection Management: Connection management becomes an important issue to be addressed as several responders may be sharing video and audio streams.

Security: Security of the NG-9-1-1-network not only needs to be maintained but also enhanced.

Privacy: Study image distortion and masking of parts of video or images to protect privacy of callers.

Social Networks as First Responders: Many times people call friends and family members first when faced with a problem. The use of social networks has made this an important addition to emergency response system. This process can make friends and family first responders in an emergency situation.

Medical Records: Provide the ability to select which responder or responders can have access to medical or personal information of the caller(s).

The next generation of communication system will have the capability of multimedia transmission and several streams being broadcasted simultaneously. FIG. 1 shows an example of such a multimedia based call scenario. As shown in FIG. 1 the smart phone running VOIP software called Sipdroid has several sensors and applications allowing video, pictures and voice transmission.

The call center may have four categories of calls for a given incident. First are individual callers. These scenarios are based on individuals calling 9-1-1 help. These individuals could range from children to elderly, English and non-English speaking, handicapped, disoriented or barely alive. Individual callers can use the traditional landline phone, cell phone or the IP phone to make a 911 call. In the case of medical emergency, new technologies can provide additional useful information to the Public Safety answering Point ("PSAP") operator to better handle the emergency. For example a caller can use the video camera on his cell phone to show the nature of emergency. Instead of a verbal description, the PSAP operator can visually see the problem. A caller who is handicapped and cannot speak can use text messaging or also the cell phone camera (image or video) to show the problem. This can better assist in a two way communication as the PSAP can visually see if the caller is following the instructions given by the operator.

Second are Third Party Services. These scenarios are based on calls made by Services like OnStar that monitors vehicle crashes, alarm companies that monitor break-ins, fires or other emergencies, home monitoring services of medical devices for people, and services that monitor infrastructures like highways, bridges and water ways. These services are dependent on sensors alerting them about the problem. Many times the alert by the sensors is followed by a call to some person to confirm the emergency, for example a call to the home owner in case of a break-in alert. These services in turn then call the appropriate 911 service to handle the emergency. While the advantage of these services is that it cuts down on the number of false alarms, the disadvantage is that it also causes a delay in handling the emergency. In this case also new technology can help. Direct feed of a video camera to the PSAP would help. The third party operators should be able to route a video feed to 911 PSAP.

Third are calls from Emergency Response Units in the field. These scenarios are based on situations where the units that respond to emergency require additional support. Some of the examples of these situations are when medical personnel responding to an emergency situation need support of law enforcement personnel if the situation turns dangerous, or fire station responders might discover some illegal activities or police officers responding to a vehicle crash might call medical services for help. When follow up units are responding to a crisis, video technology can be used to relay images of the scene to all units. The PSAP operator can better coordinate the response of individual units if there is a video display at PSAP as well as a display with each unit.

Finally, the fourth category is automatic calls based on sensors. These are scenarios where a fusion of data from different sensors results in an automatic 9-1-1 call. One possible scenario could be sensors detect chemical spills and automatically notify emergency services. Another example could be vehicle sensors transmitting information about the state of the vehicle (rollover or not).

The network architecture will have to consider not only the new VoIP scenarios, but also needs to be backward compatible. The legacy networks and the wireless networks will also be operational in several jurisdictions simultaneously. So a 911 call may go over one or more of these networks before reaching its destination PSAP.

The increase in bandwidth of telecommunications networks allows the possibility of several streams of data simultaneously transmitting information in real time. On the other hand the sensor technology has matured to a point where they are embedded in cell phones and other devices. The mass production of smart phones with built-in sensors such as an accelerometer, a camera with flash and a microphone sensor makes them valuable to the biomedical domain. It is possible for these sensors to automatically transmit information that they detect about a specific medical condition. These sensors may be used in dedicated medical devices that people can wear on their person to help them diagnose a specific medical condition. For example there are devices that help people track their daily blood pressure. Or the sensors may be embedded in more general personal devices like the cell phones. In emergencies, the callers may be physically or cognitively impaired and these dedicated devices may not be readily available. In such situations the sensors in the cell phones, which are readily available, may be used to detect and automatically transmit useful information. This section describes some of the applications that help in measuring certain vital signs of the human body. These measurements may not be very accurate and are not meant to replace the actual medical devices. The focus is on the fact that while actual medical help arrives for help, these devices can help the Para-medical people prepare for the medical emergency.

A continuous feed of patient's vital signs to the first responders and the hospital is important. It is also important for the hospital receiving the patient to know the approximate time of arrival of the patient. Wireless sensors and modern networks can help in communicating this information (UK Department of Health 2005). One of the advantages of video streaming is live information sharing amongst several people. For example the video stream from the scene may be seen by the dispatcher and simultaneously seen by the first responders. A study performed concluded that the live video feed to responders and at the command center was very useful (SAMU France online study). There have also been other proposed designs of multimedia based emergency services (Nena.org NG911 project online).

The current emergency Dispatch Protocols have been designed with the assumption that 911 calls are voice calls. The dispatchers have a limitation of not having direct access to the affected persons. They have to rely a lot on the communication and interrogation skills to elicit optimum information from the caller. The Dispatch Protocols are a document that consists of written, step by step, instructions for the dispatcher on how to gather information about the emergency and then follow it up with instructions on what to do for each situation. This may include giving comfort to the caller, if he or she is the affected person. It may also include giving some first aid advice and instructions to the caller, before the emergency help arrives. These protocols are almost like an algorithm for each situation. They continue to be improved and developed by the National Academy of Emergency Medical Dispatchers. However, the time to gather information is limited, and even with these protocols, there may be situations where it takes some time to reach a decision. An optimum time to make a decision is considered to be 60 seconds, also called the "Sixty second dilemma." This time was set arbitrarily, although a more reasonable time is expected to be about 75-90 seconds. It is expected that with multi-media calls, the time limit of 60 seconds may become realistic and may even be less than that.

The next generation Dispatch Protocols would use several technologies to help reduce the time it takes to help and also improve the quality of the help provided. This is achieved by better diagnosis of the problem that in turn can prepare the medical personnel to serve the patient better as he is on the way to the hospital. This reduction in time will be possible by designing the protocols so that the operator asks fewer questions. The number of instructions given to the caller is also reduced.

The following is an example of questions asked by the dispatcher for a 911 call. The corresponding change in the protocol is also given at the same time. The caller complains of chest pain and possible heart problems for a patient. The first question that the dispatcher asks is "Is the patient alert?" A modified protocol would not need to ask this question. The smart phone will have sensors to relay this information directly to the dispatcher. Given a video call, the dispatcher could also observe the patient for himself. The most instructions a caller would receive would be to move the cell phone camera to view the patient. The follow up question under old protocol is to find out if the patient is breathing normally. This question becomes redundant given the new technology There are several sources from which the dispatcher can make this conclusion about breathing without having to ask the caller. The cell phone accelerometer can determine the breathing pattern. An audio transmission of breathing sounds can be used to conclude the quality of breathing. For example, a noisy breathing pattern may be due to asthmatic problems.

According to the above example, the dispatcher will have input from several sources for a given call. The display screens for the dispatcher may need to be modified. A proposed screen layout would allow the screen to receive multiple video streams. These streams could be coming from the caller, the dispatch team, and potentially other sources. Similarly the image windows on the screen can display simultaneously a patient's medical history as sent from some remote location. In addition there is facility to receive text and email messages. A part of the screen could also display a map of the location from where the 911 call is made.

Various methods of measuring and transmitting vital signs of a human using mobile phones are described. A mobile phone based blood pressure estimation technique is described herein that replaces the traditional cuff and stethoscope traditionally used for blood pressure measurement with a combination of the mobile phone's built-in microphone and camera.

In particular, a differential technique of estimating blood pressure with the heart beat and pulse data obtained from two mobile phones is described. The procedure consists of first synchronizing the time on both the phones using a program such as Bluetooth. Then the heart beats and pulse signals are obtained using the phones. The systolic and diastolic pressure is determined by computing the pulse pressure and the stroke volume from the data recorded. By comparing the estimated blood pressure values with those measured using a commercial blood pressure meter, encouraging results of 95-100% accuracy were obtained.

DETAILED DESCRIPTION OF PREFERRED EMBODIMENTS

Figure 1:
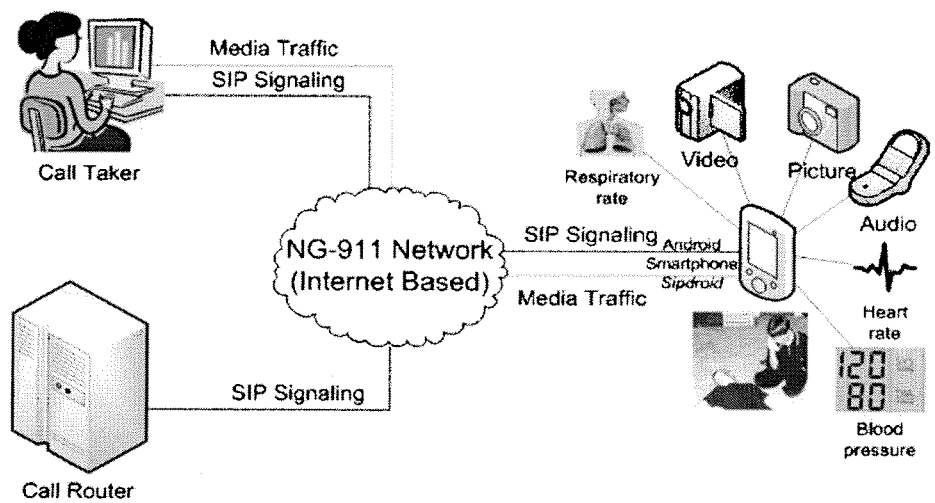
FIG. 1 shows a schematic diagram of a multimedia based call scenario utilizing Next Generation 9-1-1.

Generally, the present disclosure relates to improved 911 services and emergency dispatch protocols utilizing sensors and applications available on mobile phones. This disclosure also relates to measurement of vital signs of a human using mobile phones, including a method for estimating blood pressure utilizing a mobile phone equipped with sensors and applications.

With the advent of new telecommunications technologies such as wireless and the Internet, it has been made possible to use multimedia services for 911 rather than strictly voice services for 911 calls. The new services can use images, video and text transmissions in addition to the traditional voice transmission. The architecture for these enhanced services, called Next Generation 911 services (NG911), has been under development since 2005. The central point of interaction for 911 calls is the dispatcher at a 9-1-1 center who receives the emergency calls. The dispatcher has to respond to the emergency in an appropriate manner within a very short time. This involves asking specific questions from the caller to infer the type of emergency and then to decide on a course of action. Protocols provide a method to standardize this process across all 911 emergency centers. The operators handling the 911 calls use standard protocols, called Dispatch Protocols, to answer the calls for help. These protocols guide the operator about what questions to ask and what actions to take during a given emergency. The existing Dispatch Protocols assume a voice-only call for 9-1-1.

With the deployment of NG911, the Dispatch Protocols can be modified to make use of the multimedia calls to make the process of answering 911 calls more efficient. The new technology turns mobile phones into personal devices with several embedded sensors. In the present disclosure, the sensors in a mobile phone are used for collecting vital signs and transmitting them to the 911 dispatcher. For example, an accelerometer, embedded in a cell phone, can be used to measure the breathing rate of a person with about 90% accuracy, or it can be used to guide a person to give proper CPR in case of emergency. Similarly, the cell phone sensors can be used to get the readings of heart rate with an accuracy of about 90%. This can further enhance the effectiveness of the Dispatch Protocols by reducing the time to respond to an emergency.

The effectiveness of the improved dispatch protocols will be dependent upon several different factors. One of the most important measures of the success would be the reduction in time it takes for an operator to decide the level of seriousness of the incident and dispatch help. Another factor is the number of transactions involved. Many questions that an operator has to ask the caller during a voice call may become redundant in a multimedia call using video. So the number of questions eliminated is another measure of effectiveness. Another factor is bandwidth. Many of the vital signs may be measured by the cell phone sensors and can also be automatically transmitted. The amount of such data that can be automatically sent to the operator would be another measure. The quality of decision making and quality of service at the dispatch center are factors that should also improve. This can be measured by several factors like a reduction in the number of un-needed dispatches, and an increase in the number of lives saved.

The cost factor is also important from the call center point of view. Currently the call centers are equipped for voice only calls. A setup that allows multi-media calls would require substantial additional investment for call centers. This would include equipment costs as well as training costs.

A 911 call may be made by the affected people themselves. Such people may be facing cognitive impairment or even physical impairment. The operator answering the call goes through several steps during the call. During a voice call, the operator is dependent on the caller to give an accurate description of the problem and answer all the questions correctly. The operator may then have several instructions for the caller to help him while the dispatch personnel arrive at the scene. The operator is again dependent on the caller to follow the instructions. The operator does not have an easy way to judge if the instructions are being followed accurately or if they are helping. But in the case of a video call, the operator can follow the caller much more easily, can see the scene of the incident, and can also see if the instructions are being followed.

In situations where the caller is a close relative or friend of the affected person, the caller may have cognitive impairment. In these situations using a multimedia call, including the video would help the operator make better decisions. The operator can actually see the scene as he guides the caller while the dispatch team is on its way.

Power management may become an important issue during a multimedia phone call. If the video camera is on during a 911 call, the power consumption increases substantially. A camera can use 25% of the CPU's capabilities when the camera is being operated. It is important that the phone does not run out of battery, resulting in loss of connection. This implies a prudent use of the video camera or other features of the camera that consume power. Basically, the only way to ensure this is to use the video features for short duration as and when needed. The operator has an important role to play in this. It is the operator who can guide the caller about when to turn on the camera and when to turn it off. If the camera can be remote controlled for these features then it makes it easier for the operator to turn it on or off based on the need.

Some of the vital signs that can be recorded or otherwise monitored and relayed to the dispatcher include heart rate, respiration rate, respiration difficulty, the effectiveness of CPR being administered, and other general activities that can be detected using video. The dispatcher can also have the ability to remotely control the mobile phone being used in order to better isolate those features being examined.

EXAMPLE 1

Heart Rate

Heart rate ("HR") is a vital sign of human health. To measure HR requires a trained person or device placed at specific place on the body. Using a cell phone to measure HR may seem difficult, but there are applications that have been developed that help in reasonably accurate measurement. One of these applications is based on the concept of Photo Plethysmography ("PPG"). It uses the camera and the LED flash available on most cell phones. The principle is that every heart beat results in pumping the blood through the blood vessels, including the capillaries at the finger tips. This results in variation in light intensity that passes through the finger tips. When a finger is placed on the camera lens of a cell phone and the LED flash its utilized, a video is captured of the light passing through the finger tip. An analysis of the changes in the pattern of this light intensity is made, giving the heart rate with an accuracy of at least 95% (NENA i3 Technical Requirements Document).

Figure 2:
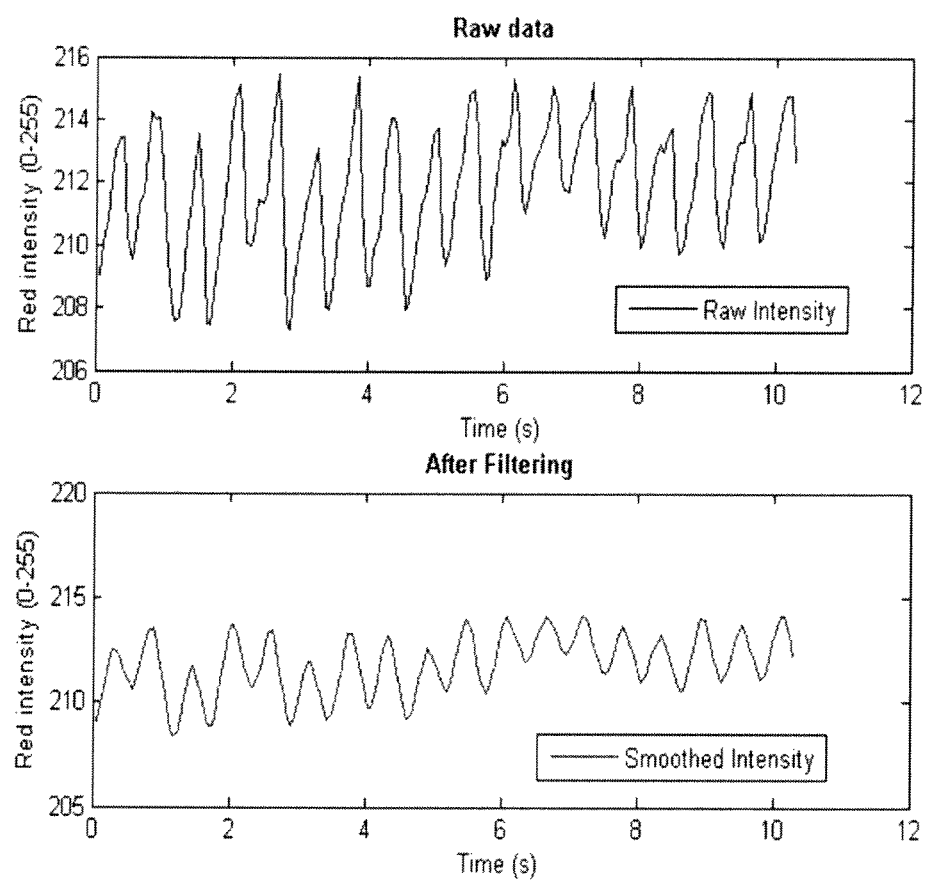
FIG. 2 shows plots of heart rate measurements taken from video analysis, both before and after filtering.

FIG. 2 shows the plot of results from video analysis for heart rate measurement, both the raw data and the filtered data. The heart rate is measured by calculating the number of peaks within a certain window frame and then using the equation:

$$HR = n*60/W_t$$

Where n is the number of peaks in the video frame and $W_t$ is the length of the frame in seconds.

The results were calibrated using a commercial heart rate monitor. In order to take readings at various heart rates, the subject had to go through different intensities of exercise. For the purpose of analysis the video frame was divided into smaller windows of 5 seconds. Table 2 below shows these readings using this method as well as the readings obtained from commercial monitor. The actual HR column shows the Heart Rate measured with a commercial HE monitor. The next 2 columns show the HR values and its accuracy when the 5 second window is used. Finally, the table shows the HR values and accuracy when a 10 second window is used.

TABLE 2

Comparison of Heart Rate Measurements

| | 5 second Window | | 10 second Window | |
|---|---|---|---|---|
| Actual HR | value | Accuracy | Value | Accuracy |
| 102 | 108 | 94.11 | 102 | 100 |
| 108 | 96 | 88.89 | 102 | 94.44 |
| 114 | 108 | 94.74 | 114 | 100 |
| 132 | 132 | 100 | 132 | 100 |
| 154 | 144 | 93.51 | 150 | 97.4 |

EXAMPLE 2

Respiration Rate and Difficulty

Figure 3:
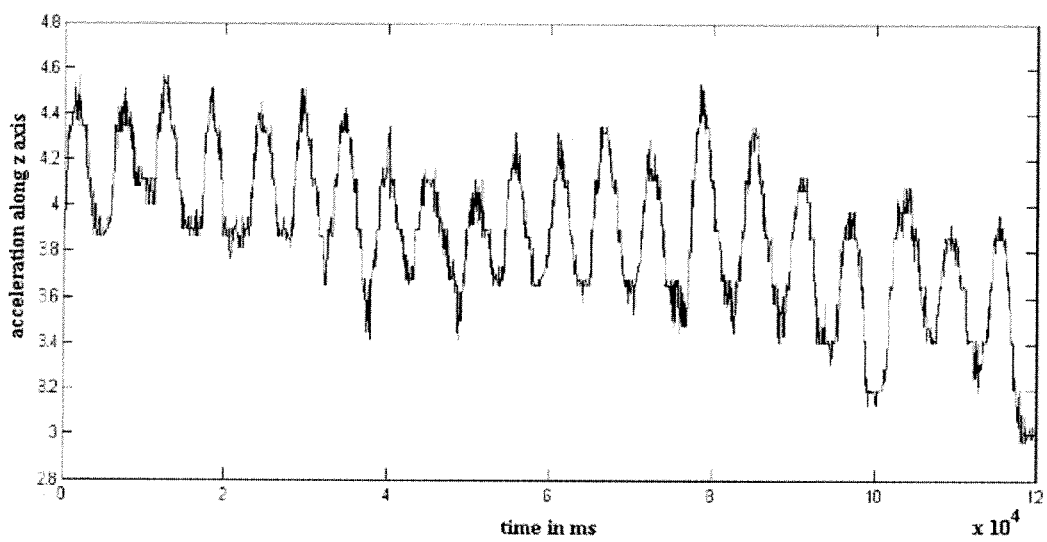
FIG. 3 shows a plot of respiration rate taken from accelerometer sensor data, indicating normal breathing.

Respiration is another important vital sign. The accelerometer sensor in a mobile phone can be used to measure the respiration rate of a person. The cell phone is placed on the upper abdomen of a person to get the best measurements for the respiration rate. It should be placed in a horizontal position, with its top and bottom parallel to an imaginary line running between the person's head and feet. The accelerometer on the cell phone records the measurement of acceleration approximately every 20 milliseconds. FIG. 3 shows a plot of the respiration as measured by the accelerometer of a cell phone. The Respiration rate can be measured with an accuracy of about 98%.

Figure 4:
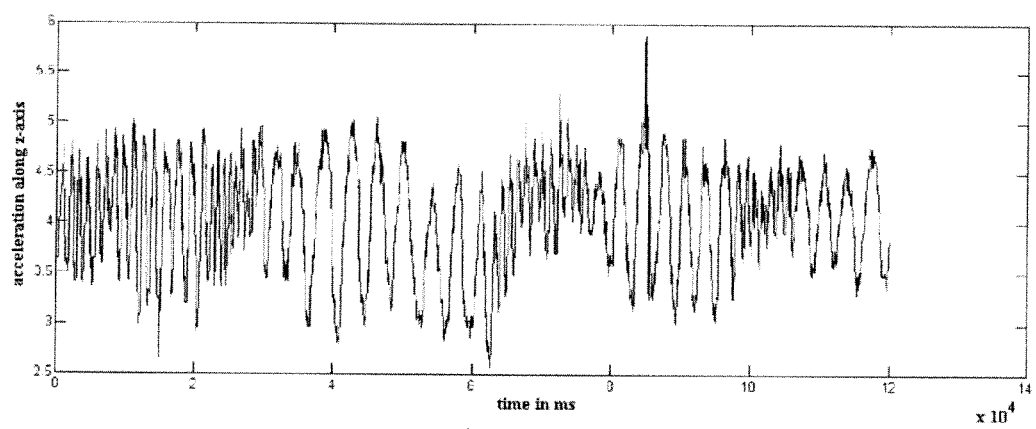
FIG. 4 shows a plot of respiration rate taken from accelerometer sensor data, indicating irregular breathing.

Another important measure of breathing is the ease or difficulty of breathing. The accelerometer graph can also indicate if the breathing is uneven. The microphone (as well as accelerometer) can capture the breathing sounds coming from the lungs if the cell phone is placed near the upper chest. This can indicate if the breathing is hard or there are any wheezing or guttural sounds coming from lungs during breathing. FIG. 4 shows a pattern of irregular breathing. The pattern shows the person breathing slow for certain period of time (about 15 times per minute) and then followed by fast breathing (bra period of time (about 45 times per minute).

EXAMPLE 3

CPR Assistance

In case of medical emergencies where the patient has stopped breathing or has a heart problem, a timely and correct administration of CPR, with appropriate frequency of chest compressions, can mean the difference between life and death. CPR needs to be given as soon as possible. Most times the people near the patient may not know how to give CPR. In such cases the 911 operator gives verbal instructions over the phone to help someone give CPR to the patient. While there are medical devices that can help administer proper CPR, these devices may not be available or accessible in emergency situations at homes or public places.

Figure 5:
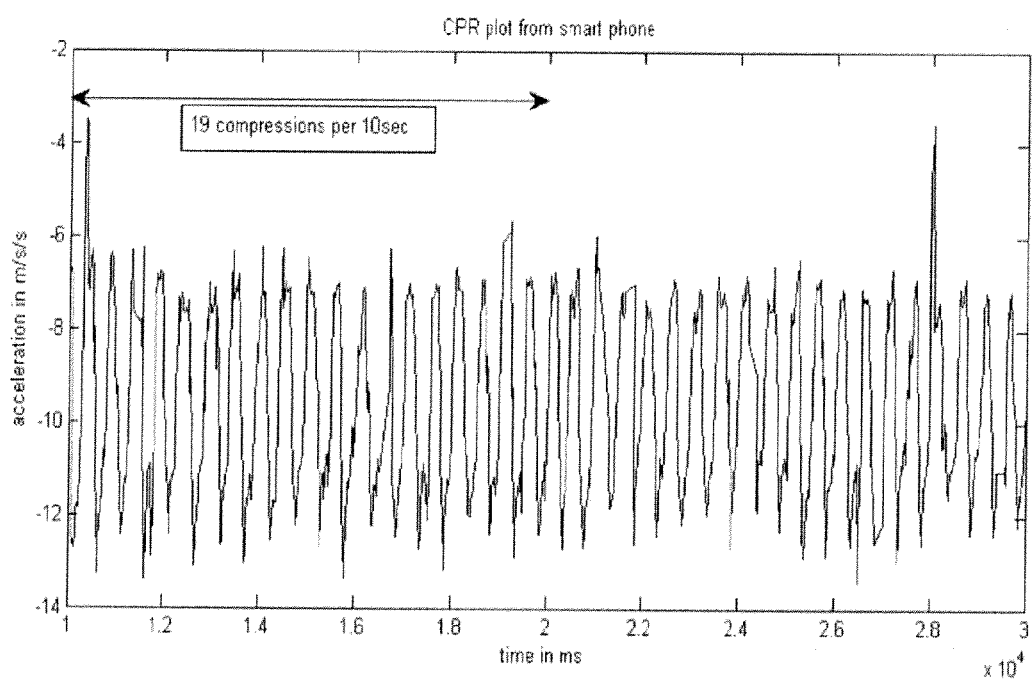
FIG. 5 shows a plot of CPR compression rate taken from accelerometer sensor data.

Here again a cell phone with an accelerometer can help in such situations. An application can be utilized that measures the frequency of chest compressions and the depth of chest compression. The application can prompt in case the person giving the CPR needs to change the frequency or depth of compression. The phone can be placed directly on the chest or can be wrapped around the hand by a cloth and then placed on the chest. FIG. 5 shows a sample of accelerometer data plot while doing a CPR.

Figure 6:
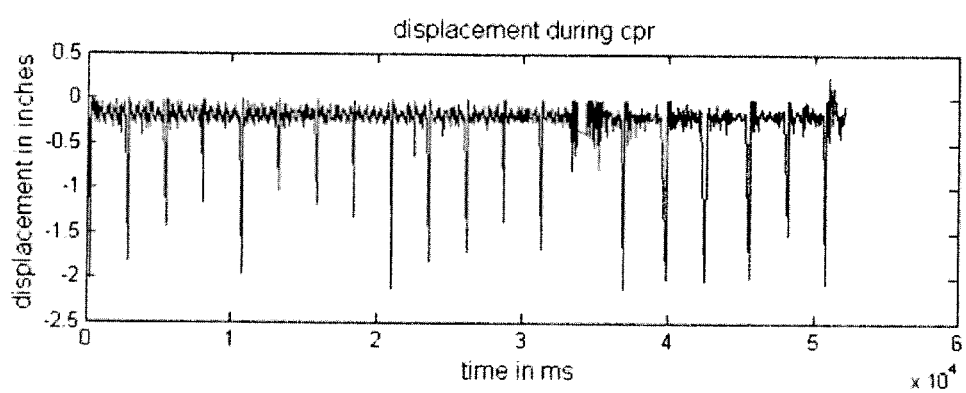
FIG. 6 shows a plot of displacement rate during CPR compressions taken from accelerometer sensor data.

FIG. 6 shows a plot of displacement during administration of CPR, as measured by a smart phone accelerometer sensor. The plot shows a regular pattern of chest compression during CPR. The calculation of displacement is done by a two step procedure. The raw data from the accelerometer gives the acceleration reading approximately every 20 milliseconds. The first step is to find the velocity by using the equation:

$$V_t = V_0 + V_d,$$

where $V_0$ is the starting velocity and $V_d$ is the change in velocity over a period of time and $V_t$ is the velocity after time t. The second step is to calculate the displacement from velocity using the equation:

$$\text{Displacement} = (V_0 + V_t)/2 * t,$$

where t is the time period.

The readings for these experiments were taken in a CPR class. Several readings were taken as the instructor performed the CPR on a Mannequin. Readings were also taken as the students performed the CPR on a Mannequin. The number of students in a class varied from 5 to 7. The experiment was done at 3 different classes. The accuracy of the plots is indicated by the fact that the instructor must perform the CPR to a depth of about 2 inches.

EXAMPLE 4

Remote Control of Sensors

On many occasions, callers are not able to operate the sensors and feed the dispatcher information about the emergency situation. In time of panic, it is also difficult for the caller to make the right observations and answer the dispatcher correctly. Because of the introduction of multimedia technology in NG911, the dispatcher should be able to extract the information about the scene by making observations and measurements remotely and should be able to instruct the caller accordingly. Table 3 below shows several ranges for different cell phone camera features. The dispatcher can remotely take control of the camera features in order to get better view of the emergency scene. This is useful when a caller is physically disabled or is cognitively impaired to the point he or she cannot effectively follow the instructions.

TABLE 3

Camera Features

| Feature | Range |
|---|---|
| Zoom | 1-40 |
| Brightness | 0-10 |
| Contrast | 0-10 |
| Sharpness | 0-30 |
| Saturation | 0-10 |
| Rotation | 0-360 |

Cell phone cameras are available with several sensors embedded in them. Many of these sensors also have controls to change their settings. For example, video cameras in a cell phone will have a setting for zooming or panning or changing the resolution of the pictures taken. These settings can be changed by using control buttons on the cell phone. Normally, the 911 operator will have to instruct the caller to change these settings, if needed. But new technology provides the ability for applications to allow the 911 operator to take control of these settings. In these cases, the operator may choose to zoom in or pan out when he feels the need for it. Similarly, the audio controls of volume may be controlled remotely if the operator is trying to listen to a breathing sound.

EXAMPLE 5

Detection of Activity

Many times, the callers/informants are not sure about the patient's state, possibly due to panic or poor cognition. It has been observed that every human activity has a direct impact on the change in bit rate associated with the frame in a video stream. The bit rates associates with various activities are shown below in Table 4. For example, in the absence of a user in the view port indicating a completely static scene, the bit rate maintains a very low value of 4 Kbps for every resolution. However, there is a change in bit rate when the scene includes a person even if the subject is completely at a standstill. The increase in the bit rate for different activities for the same resolution is due to the movement of exposed body parts involved in the activity. Hence, it can be concluded that bit rate increases even with a small amount of motion exerted by the human body without the user's knowledge. These changes are evident when a person is breathing normally and breathing heavily. It should be possible to detect even small changes in the scene, such as heavy breathing, screaming, and other body movements (using audio or video). One can extract this information in real-time without any complex image/video processing. This can help the operator make an informed decision about the state of the injured person. The dispatchers can look at the state of the person even when no one is around.

TABLE 4

Activity Detection

| Activity | KB/s |
|---|---|
| No User | 4.19 |
| Eye Blink | 24.57 |
| Smile/Scream | 20.70 |
| No Breathing | 19.06 |
| Normal Breathing | 35.11 |
| Heavy Breathing | 62.39 |

EXAMPLE 6

Modified Emergency Dispatch Protocol Questions

Table 5 below shows the typical list of emergency dispatch protocol questions asked by the dispatcher to a caller during an emergency call, depending on the nature of the reported injury. The columns to the right of the question indicate the cell phone sensor data that could be used to help answer these questions, the instructions or requests that the dispatcher could give the caller, and the quantitative data that is measured.

TABLE 5

| Current Protocol Name/ Question in Protocol | Cell phone sensor used/results | Modified question/action requested | Quantitative data |
|---|---|---|---|
| | Bleeding/Laceration | | |
| is the patient alert | Video images of moving eyes, or arms/hands, or legs. Image analysis is done. | Move the camera over the patient. Zoom or change resolution (if needed). | 1. Change in pixels values 2. Zoom in, local/remote (N times) 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate of respiration 2. Volume control, local/remote |
| Where is the bleeding from? | Video images of moving eyes, or arms/hands, or legs. Changes in pixels can lead to conclusions about limb movements | Move camera to injury. Zoom in the camera to the injury (if not possible from remote). | 1. Change in Pixels values 2. Zoom in, local/remote (N times). 3. Resolution change, local/remote |
| Is blood squirting out? | Video image of bleeding | redundant | |
| Bleeding - from where, How much, How long, Can it be controlled with pressure | Video Image of bleeding | Zoom in the camera on the bleeding. | 1. Change in Pixels values 2. Zoom in, local/remote (N times). 3. Resolution change, local/remote |
| Can the patient answer your questions? | Use of video and audio enhances the interaction | Take the phone near the patient. Increase the volume of the microphone (if needed) | 1. Volume Control, local/remote. |
| | Eye Problems/Injuries | | |
| Is the patient alert? | Video images of moving eyes, or arms/hands, or legs. Image analysis is done. | Scan the camera over the patient. Zoom in or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer remotely. Place the phone on the patient's upper abdomen. | 1. Accelerometer data for rate or respiration 2. Volume control, local/remote |
| What caused the injury? Chemicals Foreign object Impaled object Direct blow Flying object Welding/near welder | Video images of the injury and the overall scene would provide a better diagnosis of the situation. | Focus the camera over the patient's eyes. Zoom camera over the affected eye (if needed). Change the resolution (if needed). | 1. Zoom in, local/remote (N times). 2. Change resolution, local/remote. |
| Is eyeball cut open or leaking fluid? | Video image of the eyes. The zoom answers this question. | Zoom camera over the affected eye (if needed). Change the resolution (if needed). | 1. Zoom in the camera, local/remote (N times). 2. Change resolution, local/remote. |

TABLE 5-continued

| Current Protocol Name/ Question in Protocol | Cell phone sensor used/results | Modified question/action requested | Quantitative data |
|---|---|---|---|
| Are there any other injuries? | Video image of other injury, if any | Move the camera to any other injury | 1. Zoom in the camera, local/remote (N times). 2. Change resolution, local/remote. |
| Fall Victim | | | |
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio used to hear breathing sounds for wheezing etc. | Turn on the accelerometer. Place the phone on the patient's upper abdomen. | 1. Accelerometer data for rate or respiration 2. Volume control, local/remote |
| What kind of surface did the patient land on? | Video image of the surface. | Move the camera over the surface where patient fell. | 1. Zoom in the camera, local/remote (N times). 2. Change resolution, local/remote. |
| Are there any obvious injuries? What are they? | Video image of the injuries | Move the camera over the injury. | 1. Zoom in the camera, local/remote (N times) 2. Change resolution, local/remote |
| Is the patient able to move their fingers and toes? | Video images of moving eyes, or arms/hands, or legs. | Move the camera over the hands and toes of the patient. Ask him to move them. | 1. Change in pixels values. 2. Zoom in, local/remote (N times). 3. Resolution change, local/remote |
| Bleeding - from where, How much, How long, Can it be controlled with pressure? | Video images of moving eyes, or arms/hands, or legs. | Zoom in the camera on the bleeding. | 1. Change in Pixels values 2. Zoom in, local/remote (N times). 3. Resolution change, local/remote. |
| Heat/Cold Exposure | | | |
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Can the patient answer your questions? | Use of video and audio enhances the interaction | Take the phone near the patient. Increase volume of the microphone if needed. | 1. Control Volume of the microphone from local/remote. |
| If the patient is complaining of pain, where? | Video images of pain area may help better diagnosis | Move the camera over the area of pain. Zoom over the pain area, if needed. | 1. Change in pixels values. 2. Zoom in, local/remote (N times). |

TABLE 5-continued

| Current Protocol Name/ Question in Protocol | Cell phone sensor used/results | Modified question/action requested | Quantitative data |
|---|---|---|---|
| Does the patient respond to you and follow simple commands? | Video/audio interaction. Operator interacts with the patient. | Take the phone to the patient. Change Microphone Volume, If needed. | 3. Resolution change, local/remote 1. Control Volume of the microphone local/remote. |
| Is the patient sweating profusely? | Video image of the patient and image analysis helps. | Move the camera over the patient's face. Zoom in, if needed Change resolution, if needed. | 1. Change in pixels values. 2. Zoom in, local/remote (N times). 3. Resolution change, local/remote |
| Is the patient dizzy, weak or feeling faint? | Video images and data from pressure sensor on screen. | Operator asks the patient to press on the camera touch screen to measure pressure. | 1. Pressure change from touch screen. |
| Industrial Accidents ||||
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Is the patient able to move their fingers and toes? | Video images of moving eyes, or arms/hands, or legs. | Move the camera over the hands and toes of the patient. Ask him to move them. | 1. Change in pixels values. 2. Zoom in, local/remote (N times). 3. Resolution change, local/remote |
| Bleeding - from where, How much, How long, Can it be controlled with pressure? | Video images of moving eyes, or arms/hands, or legs. | Zoom in the camera on the bleeding. | 1. Change in Pixels values. 2. Zoom in, local/remote (N times). 3. Resolution change, local/remote. |
| Stabbing/gunshot assault ||||
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Is there more than one person injured? | Video images of the scene | Move the camera over the entire scene. Pan the camera, if needed | 1. Pan the camera local/remote |
| Is there more than one wound? What part(s) of the body is/are injured? | Video images of the injuries | Move the camera over all the injuries. Zoom the camera, if needed | 1. Zoom in local/remote (N times). |

TABLE 5-continued

| Current Protocol Name/ Question in Protocol | Cell phone sensor used/results | Modified question/action requested | Quantitative data |
|---|---|---|---|
| Bleeding - from where, How much, How long, Can it be controlled with pressure? | Video images of moving eyes, or arms/hands, or legs. | Zoom in the camera on the bleeding. | 1. Change in Pixels values. 2. Zoom in, local/remote (N times). 3. Resolution change, local/remote. |
| Vehicular related injuries | | | |
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Are there any hazards present? (Is the scene safe), Fire, Water, HazMat, Wires down | Video image of the scene | Move the camera over the entire scene of the accident. Pan the camera over the entire scene. | 1. Pan the camera |
| How many patients are injured? Are all of the patients free of the vehicle? | Video image of the scene. | How many patients are injured? Are all of the patients free of the vehicle? | |
| What types of vehicle(s) are involved? | Video image of the scene, focus on the vehicle | Move the camera over the vehicle | |
| Is anyone trapped in the vehicle? | Video image of the scene, focus on the injured | Is anyone trapped in the vehicle? | |
| Traumatic Injury | | | |
| Is patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Bleeding - from where, How much, How long, Can it be controlled? with pressure? | Video images of moving eyes, or arms/hands, or legs. | Zoom in the camera on the bleeding. | 1. Change in Pixels values. 2. Zoom in, local/remote (N times). 3. Resolution change, local/remote. |

TABLE 5-continued

| Current Protocol Name/ Question in Protocol | Cell phone sensor used/results | Modified question/action requested | Quantitative data |
|---|---|---|---|
| Where is the patient injured? | Video images of the injury | Move the camera over the injury | 1. Zoom in, local/remote (N times). |
| Abdominal Pain | | | |
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| How does the patient act when he/she sits up? | Make the person sit and observe on video | Move the camera showing the patient. Ask him to sit | |
| Has the Patient Vomited? If yes, what does vomit look like? | Video images of vomit can help. Number of pixels and color changes of pixels may lead to automatic conclusions. | Has the patient Vomited? If yes, Move the camera over the vomit. | 1. Zoom in, local/remote (N times) 2. Change in Resolution, local/remote. |
| Allergies Stings | | | |
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| How does the patient act when he/she sits up? | Make the person sit and observe on video | Move the camera showing the patient. Ask him to sit. | |
| Does the patient have any rashes or hives? | Video image of bite area. Increased resolution and pixel analysis would show the seriousness of the rash | Move the camera over the rash area of his/her body. Increase the resolution, if needed. Zoom the camera over the rash, if needed | 1. Zoom in, local/remote (N times). 2. Change in resolution local/remote. |
| Back Pain | | | |
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Breathing Problems | | | |
| Is the patient alert? | Video images of moving eyes, or | Move the camera over the patient. Zoom or | 1. Change in pixels values. |

TABLE 5-continued

| Current Protocol Name/ Question in Protocol | Cell phone sensor used/results | Modified question/action requested | Quantitative data |
|---|---|---|---|
| | arms/hands, or legs. Image analysis is done. | change resolution (if needed). | 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Is the patient able to speak in full sentences? | Video/Audio interaction with patient | Take the phone to the patient. Increase volume of the microphone if needed. | 1. Volume control local/remote. |
| Is the patient drooling of having a hard time swallowing? | Video images of person's face. Pixel changes would lead to automatic conclusions about drooling and swallowing problems. | Move the camera over the patient's mouth. Zoom in the camera, if needed Increase resolution, if needed. | 1. Zoom in, local/remote (N times). 2. Change in resolution, local/remote |
| Chest Pain/Heart Problems | | | |
| Is the patient alert? | Video images of moving eyes, or arms/hands, or legs. Image analysis is done. | More the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Is the patient nauseated or vomiting? Is the patient sweating profusely? | Video images of the person. Image analysis is done | Move the camera over the patient's face. Zoom in, if needed. Increase the resolution, if needed. | 1. Change in pixels values. 2. Zoom in, local/remote (N times). 3. Resolution change, local/remote |
| Is the patient experiencing rapid heart rate with chest pain? | Use cell phone sensors - accelerometer, video, audio to determine heart rate | Turn on the accelerometer. Place the camera on the patient's chest. Ask the patient to put finger on the camera lens. | 1. Accelerometer data 2. change in Pixel intensity |
| Diabetic Problems | | | |
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/ remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Is the patient sweating profusely? | Video image of the patient and image analysis helps. | Move the camera over the patient's face. Zoom in, if needed Change resolution, if needed. | 1. Change in pixels values. 2. Zoom in, local/remote (N times). |

TABLE 5-continued

| Current Protocol Name/ Question in Protocol | Cell phone sensor used/results | Modified question/action requested | Quantitative data |
|---|---|---|---|
| | | | 3. Resolution change, local/remote |
| Headache | | | |
| Is the patient alert? | Video images of moving eyes or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing | Turn on the accelerometer. Place the phone on the patient's upper abdomen. | 1. Accelerometer data for rate or respiration 2. Volume control, local/remote |
| OD/Poisonings/Ingestion | | | |
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Is the patient having difficulty swallowing? | Video images of the person. Number of pixel changes and the color changes of pixels would lead to automatic conclusion about swallowing problems. | Move the camera over the patient's mouth. Zoom in the camera, if needed Increase resolution, if needed. | 1. Zoom in, local/remote (N times). 2. Change in resolution, local/remote |
| Psychiatric/Behavioral Problems | | | |
| Is the patient alert? | Video images of moving eyes, or arms/hands, or legs. Image analysis is done. | Move the camera over the patient. Zoom or change resolution (if needed). | 1. Change in pixels values. 2. Zoom in, local/remote (N times). 3. Resolution change, local/remote |
| Is the patient breathing normally? | 1. Accelerometer data showing respiration rate. 2. Microphone audio to hear breathing sounds for wheezing etc. | Turn on the accelerometer. Place the phone on the patient's upper abdomen. | 1. Accelerometer data for rate or respiration 2. Volume control, local/remote |
| Can the patient answer your questions? | Use of video and audio enhances the interaction | Take the phone to the patient. Increase the volume of the microphone (if needed) | 1. Control Volume, local/remote. |

EXAMPLE 7

Cuffless Differential Estimation of Blood Pressure

The differential estimation of blood pressure involves the use of two mobile phones. One is for recording the heart sounds using the built-in microphone and the other is for recording the video of the pulse data obtained from the subject's finger.

Figure 7:
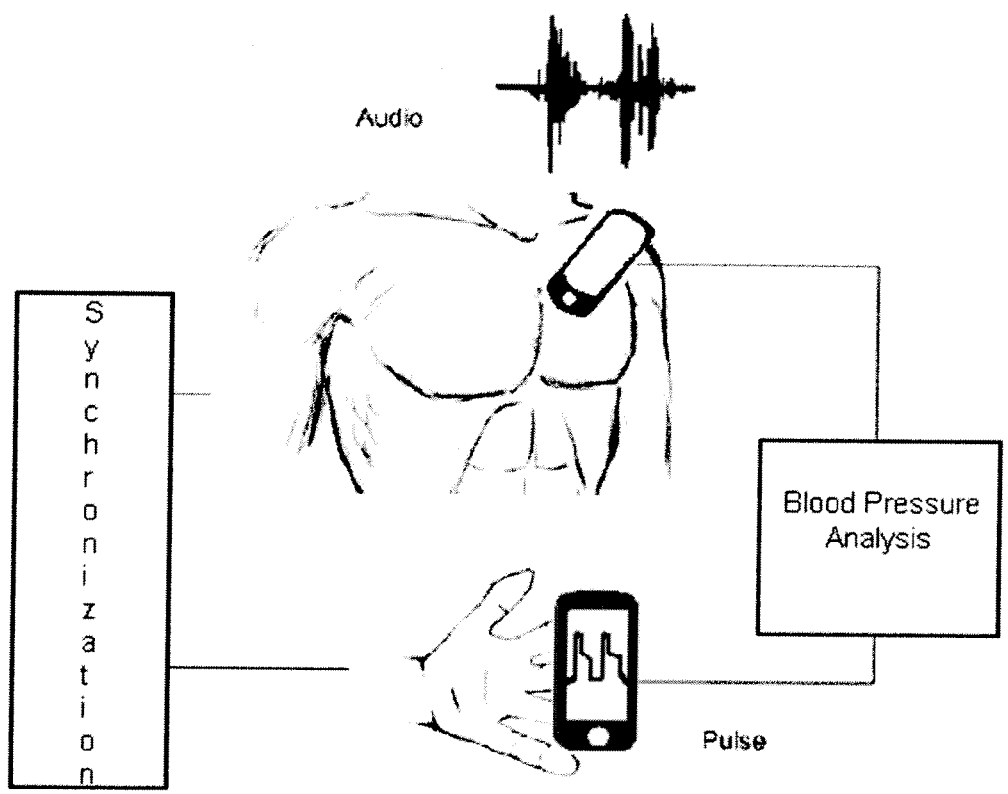
FIG. 7 shows a general scheme for blood pressure estimation according to the present disclosure.

This technique consists of three phases. First is the synchronizing of time between the two mobile phones, preferably using Bluetooth, followed by the second phase which involves locating an appropriate spot on the chest for recording heart sounds. The audio data of the heart sound is used to calculate the heart rate. The third phase involves calculation of systolic pressure, pulse pressure and the diastolic pressure. FIG. 7 shows the overall procedure of the differential estimation technique. Pulse signals are obtained using the video recording application when the finger is placed over the lens and heart sounds are recorded simultaneously using the audio application by placing the other phone over the chest as shown in FIG. 1.

The process starts with synchronization of time between two mobile phones, preferably using Bluetooth. After synchronization, the camera on one mobile phone records the pulse in the finger at 24 fps via a video recording application. An LED flash lights up when the application starts and then the start-time of video recording is saved in the phone's SD card. Similarly, the second mobile starts recording the heart sounds via the audio recording application with the phone's microphone held close to the chest. Care has to be taken that the microphone's opening is held tightly to the skin over the chest to avoid recording external noise.

Figure 8:
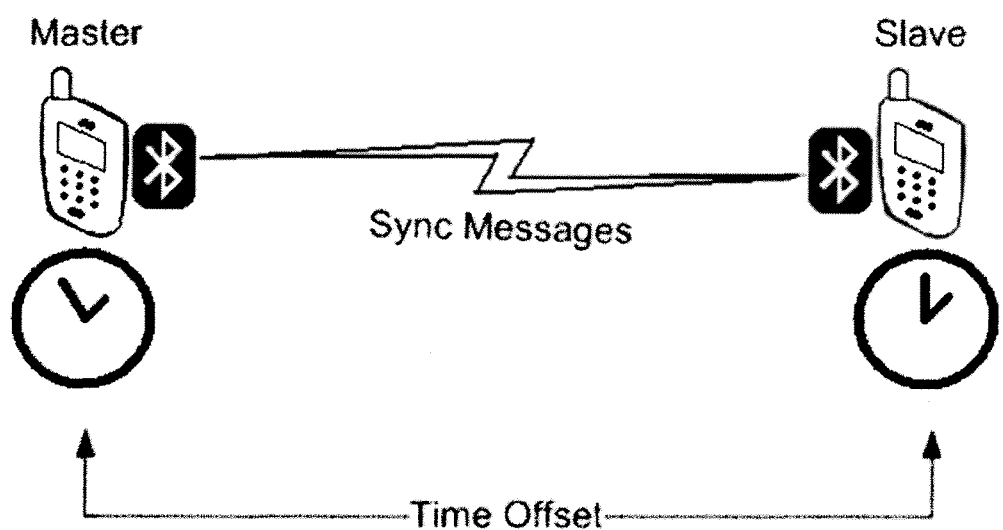
FIG. 8 shows a general scheme for synchronization of two mobile phones.

For synchronizing the clocks on both the mobile phones, a synchronization protocol was developed. This protocol is similar to the Precision Time protocol-IEEE 1588 used in wired networks. The synchronization procedure preferably utilizes Bluetooth and follows a Master-Slave architecture. The mobile phone which receives the synchronization messages acts as the master and the one sending acts as the slave. FIG. 8 shows the synchronization mechanism between the two phones. In this example, Nexus One and HTC Hero mobile phones were used running Android operating system. Any suitable phones with the necessary capabilities using any suitable operating system can be utilized. The Nexus One was equipped with a Broadcom BCM4329 chipset supporting Bluetooth 2.1+EDR (Extended Data Rate technology) along with 802.11n WiFi. The Hero supports Bluetooth 2.1+EDR along with a 802.11b/g WiFi connectivity. The phones communicated via the Android BlueZ, a Bluetooth 2.1 compatible stack capable of running on any Bluetooth chipset. The Nexus One was used for video recording and acted as the master. The Hero was used for heart beat recording and acted as the slave. The synchronization procedure consists of two steps.

Figure 9:
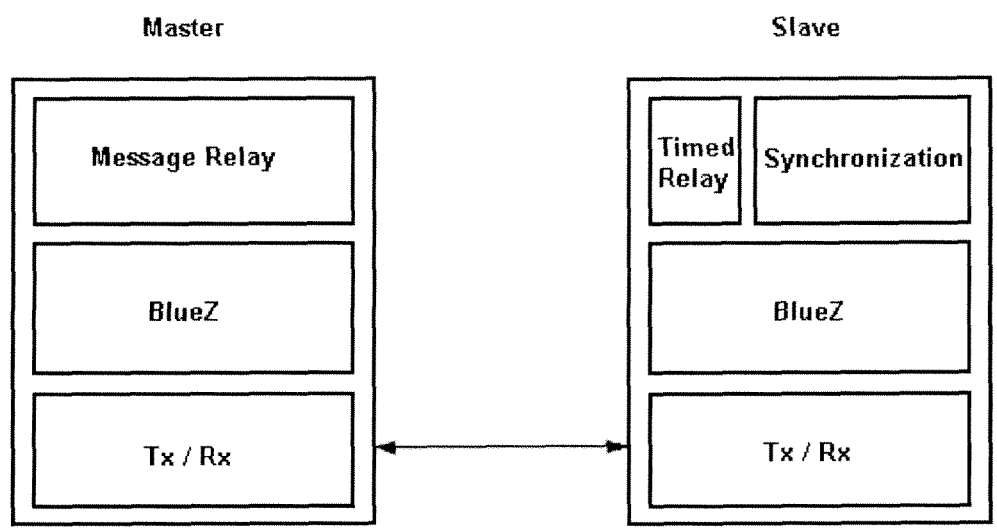
FIG. 9 shows functional components for each mobile phone during synchronization.

First is the aster-slave message exchange mechanism. The layered architecture comprises of three important layers namely Application, Bluetooth Stack and the Communication layers. FIG. 9 shows the functional components described for each layer. The master device's application layer consists of a message relay module to relay a reply message, whereas the slave's application layer consists of message relay and time synchronization modules to calculate the exact time to be set on the host device relative to the master device. The Bluetooth stack and the communication layers are the same for both the devices.

Figure 10:
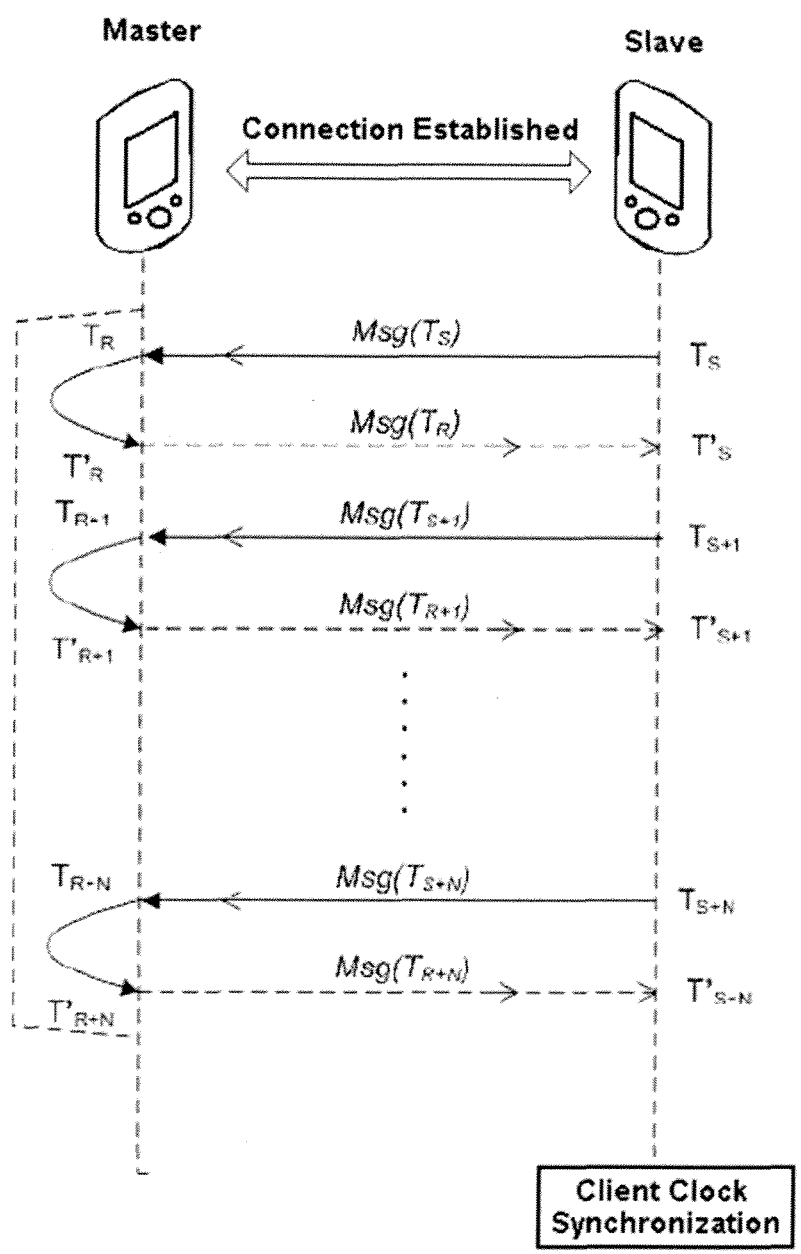
FIG. 10 shows a flow of events during synchronization of two mobile phones.
Figure 11:
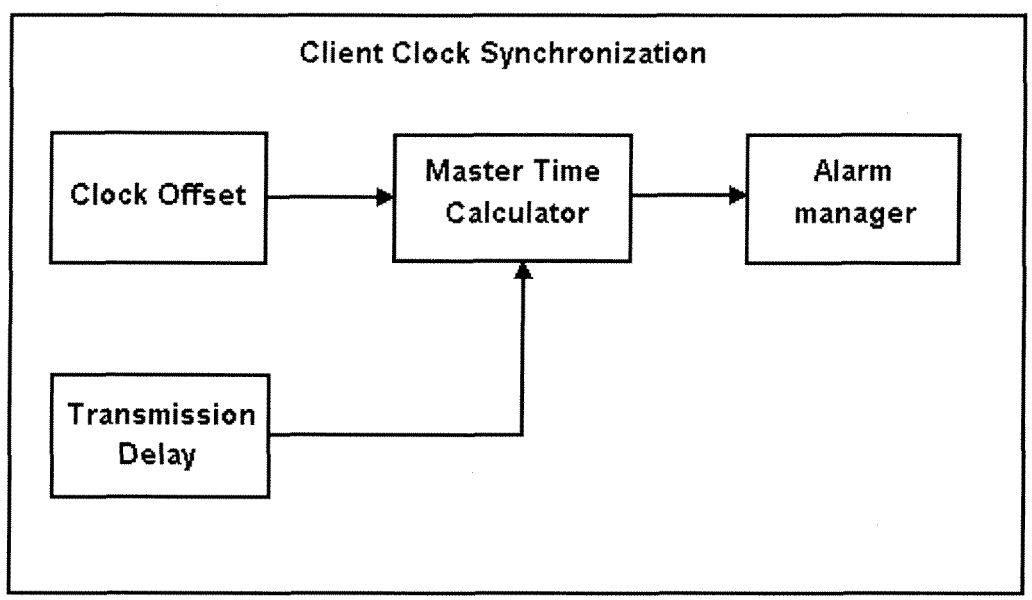
FIG. 11 shows functional components in a client clock in a mobile phone during clock synchronization.

Second is the slave device synchronization to master clock. The master device's timestamp is obtained through Bluetooth and is fixed on the slave device. This simple method synchronizes time on two devices. Differential estimation of blood pressure requires time calculations precise to milliseconds. Ignoring transmission delays will lead to degradation in the system's accuracy. Hence, transmission delays have to be calculated during the procedure. This requires the timestamps of both the systems. FIG. 10 depicts the working of the synchronization process. The first step is the standard establishment of a Bluetooth connection after pairing with the device. Once the connection is established, the slave device sends a timestamp to the master and stores it as $T_S$. As soon as the master device receives the timestamp, it sends back its own timestamp to the slave device. This returned timestamp is recorded as $T_R$ along with the timestamp when $T_R$ was received by the slave device as T0S. The process is repeated for 30 seconds and the timestamps are recorded. This process is followed by the client clock synchronization module in the slave device. This module has four major operations: estimating the roundtrip time, estimating the offset, calculating the master time, and setting the slave clock. FIG. 11 shows the components inside a client clock synchronization.

The roundtrip time is given by the following equation:

$$RTT = T'_S - T_S \quad (1)$$

The one-way transit time between the terminals is one half of the roundtrip time given by the following equation:

$$T_t = \frac{RTT}{2} \quad (2)$$

The offset between the two devices $O_t$ is given by difference in timestamp of the master and slave device according to the following equation:

$$O_t = T_S - (T_R - T_t) \quad (3)$$

Subtracting the one-way transit time from the receiving time in the master device will produce the accurate time difference between the slave and master device. The master clock time is estimated by subtracting the offset with the slave clock.

After synchronization, the next step is localization of the heart beat and pulse. Localizing a heart beat is a challenging task, but necessary for accurately determining blood pressure. A brief description of heart sounds is as follows. Heart sounds are produced with the opening and closure of heart valves. The heart produces mainly 4 types of sounds in one heart cycle denoted as S1, S2, S3 and S4. The first heart sound (S1-lub) is produced by the atrioventricular valves (i.e., mitral and tricuspid), and the second heart sound (S2, dub) is produced by the semilunar valves (i.e., aortic and pulmonary valve). The third and fourth heart sounds are produced only in some rare conditions due to gallop. In this method, only the first and second heart sounds need to be recorded. Experiments were conducted on the chest region to find the best spot for obtaining recordable heart sounds. The four locations of the valves were identified and selected for recording purposes. Based on the experiments, the heart sounds captured from the microphone were heard the loudest in the pulmonary region containing the pulmonary valve. Since the pulmonary valve is associated with the S2 sound, in most cases the decibel level of S2 is higher than that of the S1. Table 6 below gives the location of valves in the chest with respect to the intercostal space and sternum.

TABLE 6

Location of Valve on Chest

| | | |
|---|---|---|
| Pulmonary valve | second intercostal space | left upper sternal border |
| Aortic valve | second intercostal space | right upper sternal border |
| Mitral valve | fifth intercostal space | medial to left mid-clavicular line |
| Tricuspid valve | fourth intercostal space | lower left sternal border |

The third step is pulse detection and heart rate calculation. The procedure for detecting a pulse works on the principle that every heart beat pertains to a rush of blood in the blood vessels, even in the capillaries at the finger-tips (Banitsas 2009). By placing the finger over the camera and turning on the flash through a video recording application, the following observations were made. During a systolic pulse when the capillaries are rich in blood, more light was absorbed by the blood, leading to a low reflective index and darker frame intensities. Likewise, during a diastolic pulse, most of the light was reflected leading to bright frames. The change in intensity of light passed through the finger creating an alternative pattern of waves. These changes in intensity with time were used to obtain the pulse of a person.

Figure 12:
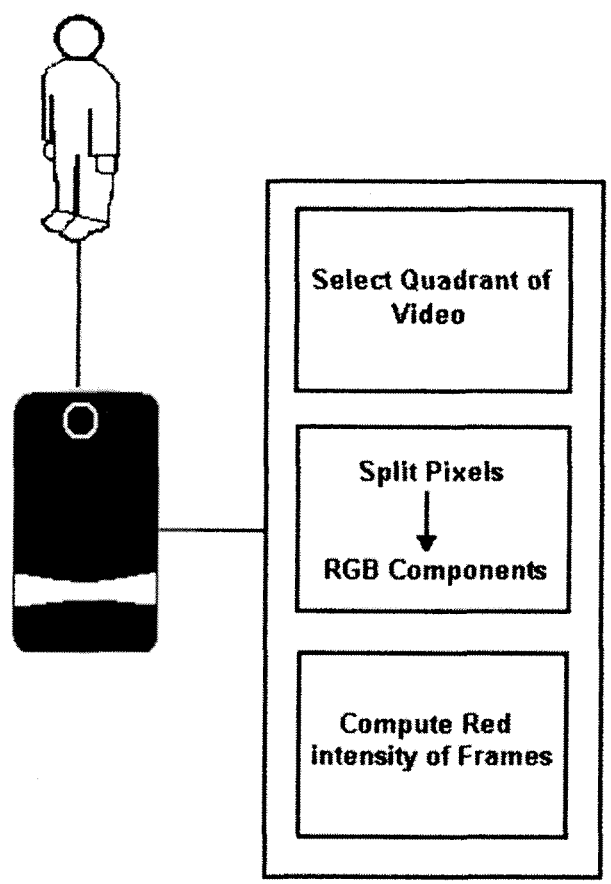
FIG. 12 shows a general scheme for deriving pulse signal from the finger tip and calculating heart rate.
Figure 13:
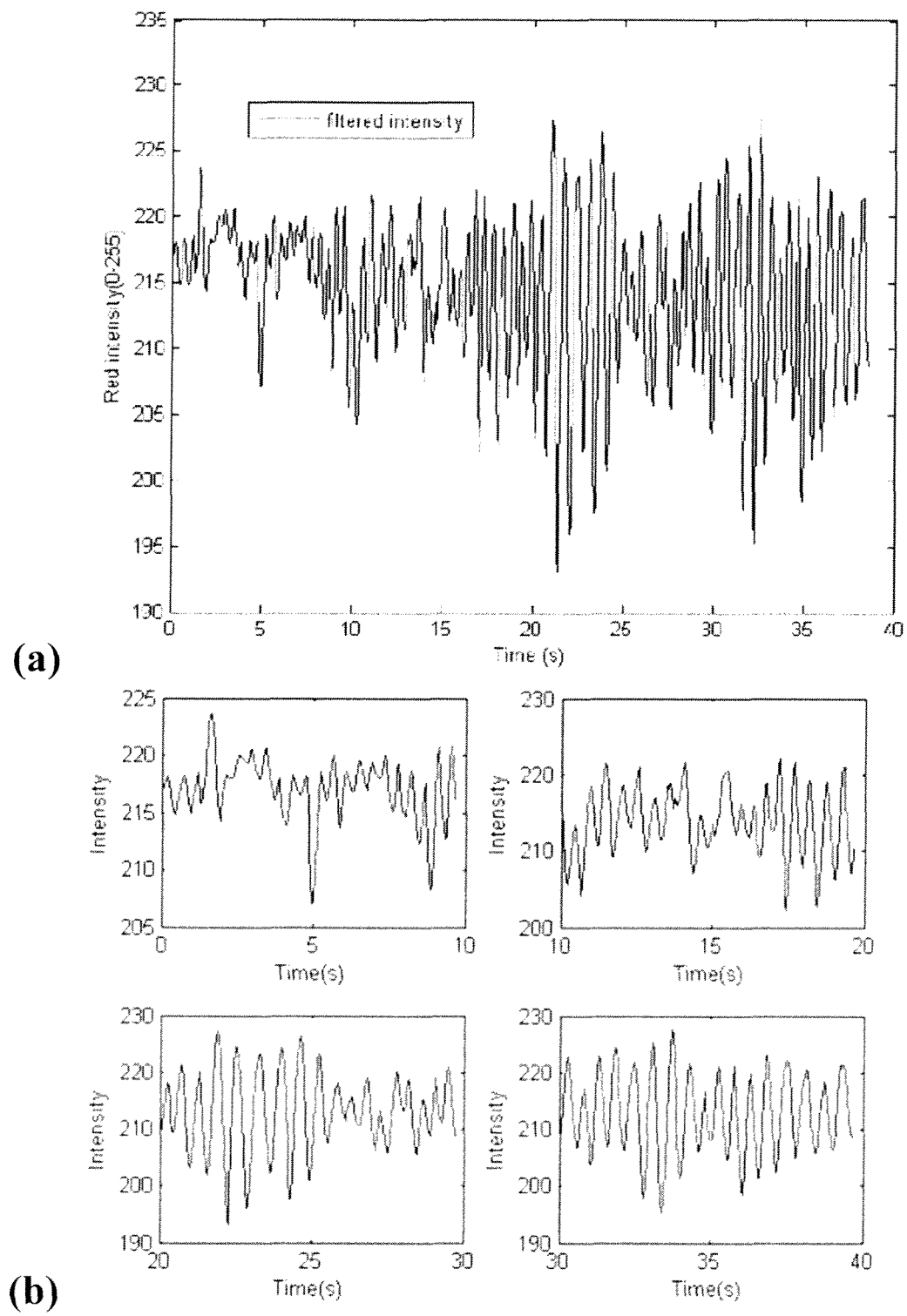
FIG. 13 shows (a) a total video data collected on pulse rate and (b) the data split into smaller time frames.

FIG. 12 depicts the procedure for deriving the pulse signal from the finger and calculating the heart rate. The pixel information from the video was split into individual Red, Blue and Green components. In most of the frames observed, the prominent color was red. Every frame of the video was split into 4 quadrants and only the first quadrant was considered for analysis because the fluctuations were more predominant in that region. Then the frames were split on a fixed length window (Wt) to check for the number of peaks (n) occurring at equal intervals of time as shown in FIG. 13. FIG. 13(a) shows the total window of data, while FIG. 13(b) shows the data split into smaller time frames. The heart rate ("HR") was calculated by using the following equation:

$$HR = (n*60)W_t \quad (4)$$

Figure 14:
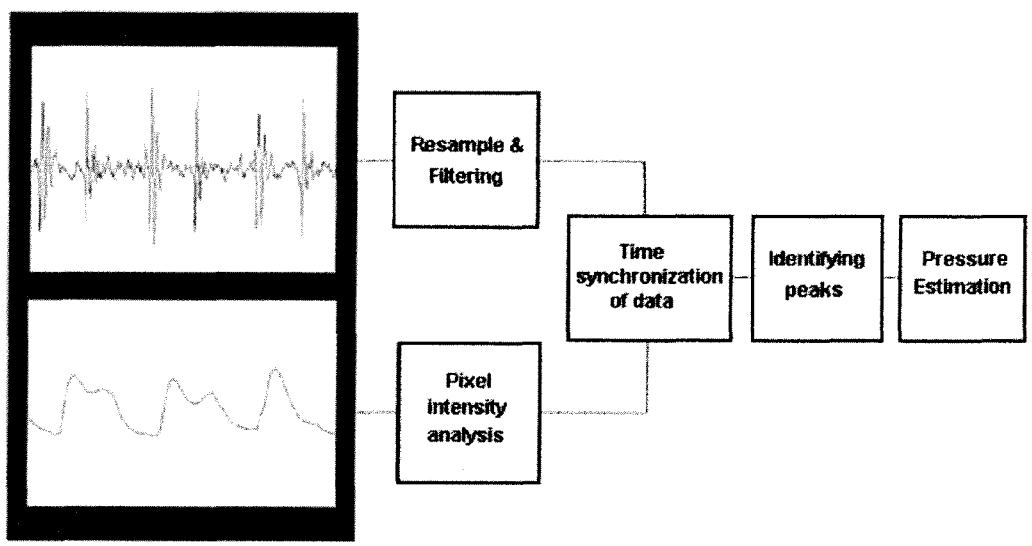
FIG. 14 shows a general scheme for sequential execution of events during blood pressure estimation.

FIG. 14 illustrates the sequential execution of events in the estimation process. The estimation process starts by first synchronizing the system clocks of both the mobile phones. After this, each mobile starts recording the appropriate data. In the example, the Nexus One recorded video at a rate of 24 fps and the HTC Hero recorded audio at a sampling rate of 8 KHz. Both the mobile phones should start recording within 10 seconds after clock synchronization. Otherwise, letting the application to run for a long time creates adrift in the system clock as the processor is responsible for maintaining the system time. Moreover, when the CPU is loaded with high-priority processes, the processor cannot maintain the clock's accuracy.

In the example, all the measurements were taken for a duration of one minute with the video starting roughly five seconds after the audio. The data collected was processed offline. The first step was the denoising of data and resampling. Audio data collected from the mobile phone was passed through a 15th-order low-pass butterworth filter which allows frequencies only between 10-250 Hz since most heart sounds recorded are present within the 10-250 Hz frequency band. For computational effectiveness, the filtered audio was resampled to a lower rate of 1 KHz. Similarly, the video frames were processed as explained above to give the value of red intensity.

Figure 15:
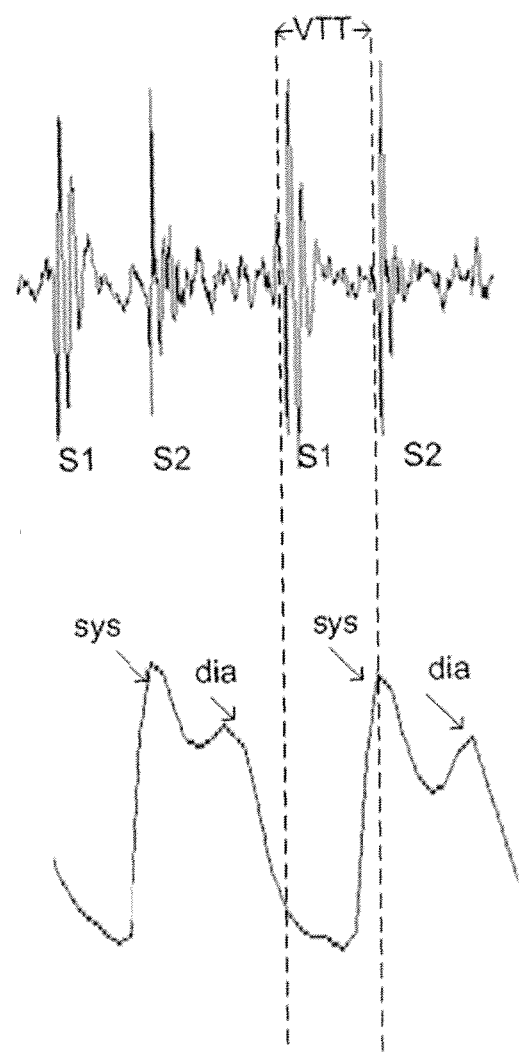
FIG. 15 shows an analysis of identified peaks in captured data pertaining to blood pressure.

The next step was determination of peaks from the data and identifying appropriate peaks in the video corresponding to the audio signal. In all the experiments, the recording process on both the phones did not start at the same time. In other words, both the audio and video data were not synchronous with the starting time. To identify peaks, the waveforms had to be aligned. To achieve this, the starting times of the recording were stored on the SD card of the two phones respectively as time stamps for calibration. For instance, suppose the starting time of the audio data was SS and the starting time of the video data was SV. The difference in the time stamps will give the amount of time one data was ahead/lagging the other. Algorithm 1 below explains the procedure followed in calibrating the two devices. Since the sampling frequency for audio was 1 KHz, adding and deleting data points was easier and more precise in audio than video at 24 fps. FIG. 15 illustrates the aligned data and how the peaks are identified. In FIG. 15, sys represents the systolic peak of the pulse 45 and dia represents the diastolic peak of the pulse. S1 and S2 are the first 46 and second heart sounds respectively. VTT is identified by time difference between the dotted lines.

---

Algorithm 1 Calibration for Synchronous start of Data

INPUT:Timestamps of Audio and Video Start ($S_S$ and $S_V$)
OUTPUT:Synchronous audio data
SyncStart = $S_S$ − $S_V$
if SyncStart ≥ 0 then
    Add Null data for SyncStart milliseconds towards start of the audio data set
end if
if SyncStart < 0 then
    Delete data for SyncStart milliseconds from the start of the audio data set
end if

---

For systolic pressure, the time of arrival of S1 and the time of arrival of the corresponding systolic peak are noted. The difference in these two time of arrivals yielded a parameter called Vascular Transit Time (VTT). VTT is defined as the dotted lines, or time taken by the blood to travel from the heart to an extremity of the body for one stroke of the heart. The change in systolic pressure can be derived from the change in VTT with respect to a reference value as shown in the equation below (Foo et al. 2006). Hence the reason for calculating VTT.

$$\Delta P_s = -0.425 \times \Delta VTT \quad (5)$$

Based on Equation 5, the systolic pressure values corresponding to the VTT can be generated. Thus, the systolic pressure is given by the following equation:

$$P_s = -0.425 \times VTT + 214 \quad (6)$$

The pulse pressure (Pp) and the stroke volume (SV) were computed as follows. For stroke volume, the following equation was used:

$$SV(mL) = -6.6 + 0.25 \times (ET-35) - 0.62 \times HR + 40.4 \times BSA - 0.51 \times Age \quad (7)$$

where ET(ms) is the ejection time and BSA is the Body Surface Area given by the following equation:

$$BSA = 0.007184 \times Weight^{0.425} \times Height^{0.725}$$

Figure 16:
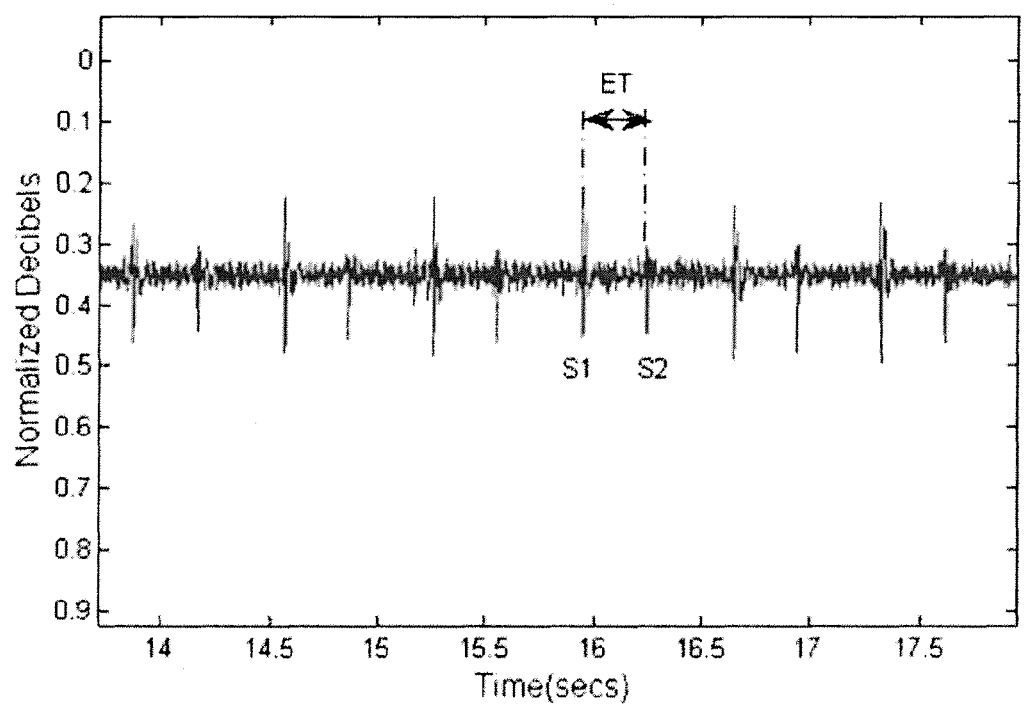
FIG. 16 shows heart beat data recorded with a microphone of a mobile phone.

Ejection time is defined as the time of ejection of blood from the left ventricle beginning with the opening of the aortic valve and ending with closing of the aortic valve. The ejection time was estimated graphically from the heart sound recorded as shown in FIG. 16. The identification of the two sounds, namely S1 accompanied by opening of the aortic value and S2 accompanied by closing of the aortic value was explained above. As shown in FIG. 16, the time difference between S1 and S2 sounds recorded using the microphone is taken as the ejection time.

With the computed stroke volume, the pulse pressure was calculated in units of mmHg using the following equation:

$$P_p = \frac{SV}{(0.013 \times Wt - 0.007 \times age - 0.004 \times HR) + 1.307} \quad (8)$$

Having obtained $P_s$ and $P_p$, the diastolic pressure ($P_d$) was calculated from the following equations:

$$P_s = P_m + \frac{2}{3}P_p \quad (9)$$

$$P_d = P_m - \frac{P_p}{3} \quad (10)$$

Subtracting Equation 10 from 9 and rearranging, the diastolic pressure is calculated from the following equation:

$$P_d = P_s - P_p \quad (11)$$

Figure 17:
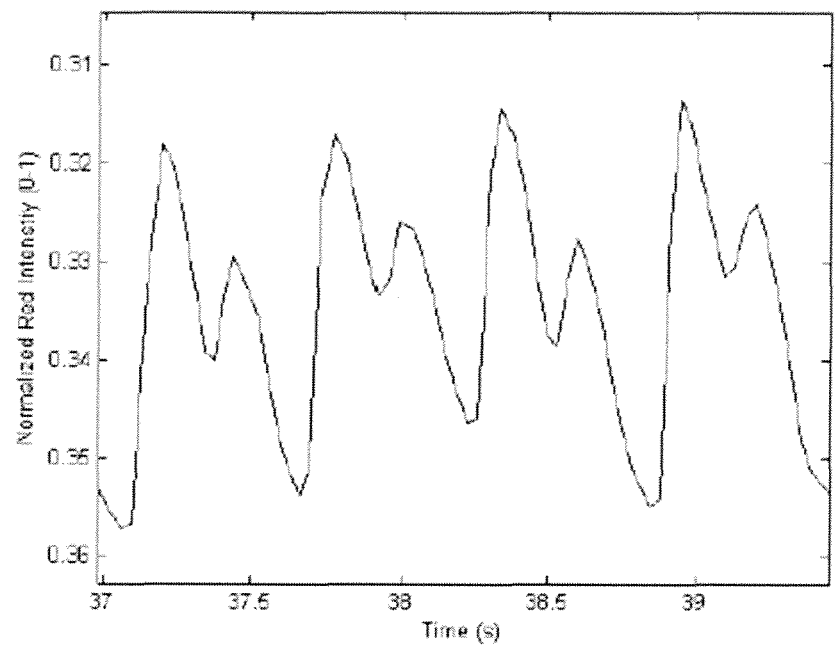
FIG. 17 shows (a) data collected for blood pressure estimation having sharp peaks, and (b) data collected for blood pressure estimation showing a pattern of flat peaks.
Figure 17:
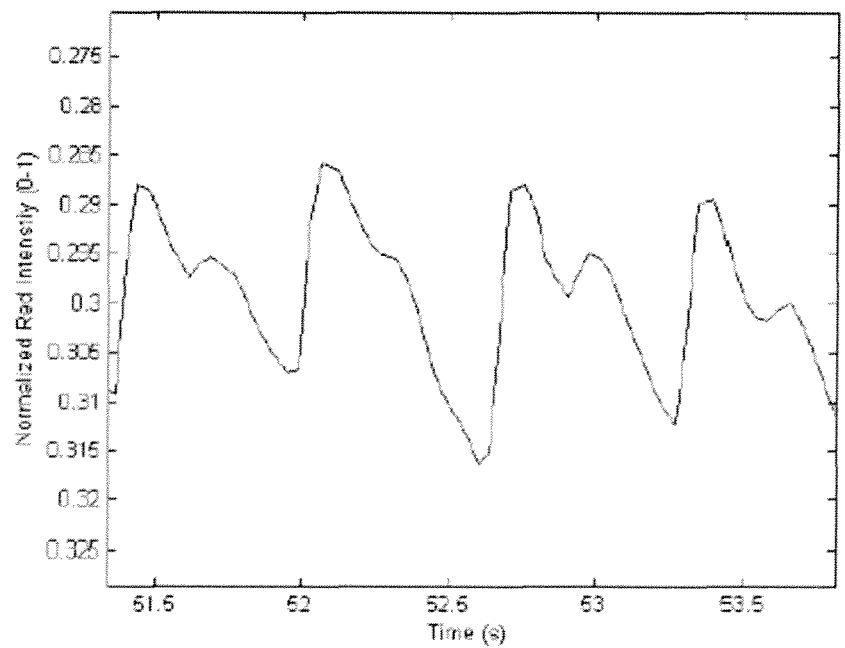

The accuracy of the results relies entirely on the effective estimation of VTT from the graphs. Identification of the time instance of S1 sound from the audio was an easy task with proper filtering of the signal, but the selection of the corresponding peaks in the video intensity was difficult in some situations due to presence of flat peaks instead of a sharp peak for a systolic pulse in the video intensity plot. The flat peak pattern appears due to the sampling error in the video. This created some confusion in the selection of a data point. FIG. 17(a) shows a plot with sharp peaks and 17(b) shows a pattern of flat peaks. A sample data set was considered and the VTT was obtained using both sharp and the flat peaked data points. Table 7 below shows the values of VTT and $P_s$ computed from a single sharp peak data point and from a series of points present in a flat peak as two columns respectively. For verifying the $P_s$ estimated using this method, the blood pressure was measured as 113 for a single subject using a commercial meter. From Table 7, it appears that using a sharp peak, the VTT varied within a small range and the $P_s$ estimated was closer to the measured blood pressure, whereas, with flat peaks there was a broad range of variation in the VTT and a considerable difference between the estimated and the measured values. The median systolic pressure was 112 for the selection of sharp peaks and 116 for flat peaks. Hence for an accurate measurement of pressure, the selection of data points plays an important role.

TABLE 7

| Sharp peak | | Flat peak | |
|---|---|---|---|
| VTT | Ps (mmHg) | VTT | Ps (mmHg) |
| 240 | 112 | 227 | 118 |
| 238 | 113 | 227 | 118 |
| 244 | 110 | 272 | 98 |
| 242 | 111 | 240 | 112 |
| 247 | 109 | 248 | 109 |
| 241 | 112 | 222 | 120 |
| 235 | 114 | 228 | 117 |
| 245 | 110 | 234 | 115 |
| 245 | 110 | 230 | 116 |
| 240 | 112 | 229 | 117 |

Table 8 gives the accuracy of results upon selection of a sharp peaked data. The measurements were collected from five individuals multiple times. This data was to used to estimate the blood pressure using the proposed method. The systolic pressure was also measured using a blood pressure meter. The accuracy is defined according to the following equation:

$$\text{Accuracy} = \frac{Md(P_s) - Es(P_s)}{Md(P_s)} \quad (12)$$

In the equation, measured (Md) $P_s$ is the pressure measured using a commercial blood pressure meter and Estimated (Es) $P_s$ is the pressure estimated as explained above. In Table 8, it can be seen that accuracy values varied between 90-100%. Also, the current method yielded an accuracy above 95% in 85% of the data sets and of 90-95% in 15% of the data sets analyzed.

TABLE 8

| Md Ps | Es Ps | Accuracy % | Md Ps | Es Ps | Accuracy % |
|---|---|---|---|---|---|
| 110 | 110 | 100 | 97.4 | 124 | 124 | 100 | 95.5 |
| 115 | 112 | 99.1 | 111 | 116 | 93.8 |
| 108 | 107 | 94.2 | 113 | 120 | 91.8 |
| 104 | 110 | 98.3 | 110 | 119 | 99.1 |
| 118 | 116 | 95.0 | 112 | 113 | 96.5 |
| 121 | 115 | 96.4 | 114 | 110 | 99.1 |
| 112 | 116 | 97.3 | 112 | 113 | 93.3 |
| 110 | 113 | | 97 | 104 | |

Accuracy of diastolic pressure is defined similar to Equation 12. Table 9 below shows the accuracy for diastolic pressure calculated. The diastolic pressure is approximated based on the amount of blood in the person for his age, calculated from ET. The accuracy may change in the case of blood loss or deficiency of blood due to abnormality.

TABLE 9

| Md Pd | Es Pd | Accuracy % | Md Pd | Es Pd | Accuracy % |
|---|---|---|---|---|---|
| 64 | 68 | 93.75 | 70 | 73 | 95.7 |
| 61 | 66 | 91.8 | 65 | 70 | 92.3 |
| 54 | 59 | 90.7 | 73 | 78 | 93.2 |
| 83 | 82 | 98.8 | 63 | 67 | 93.7 |
| 81 | 83 | 97.5 | 61 | 68 | 88.5 |

Figure 18:
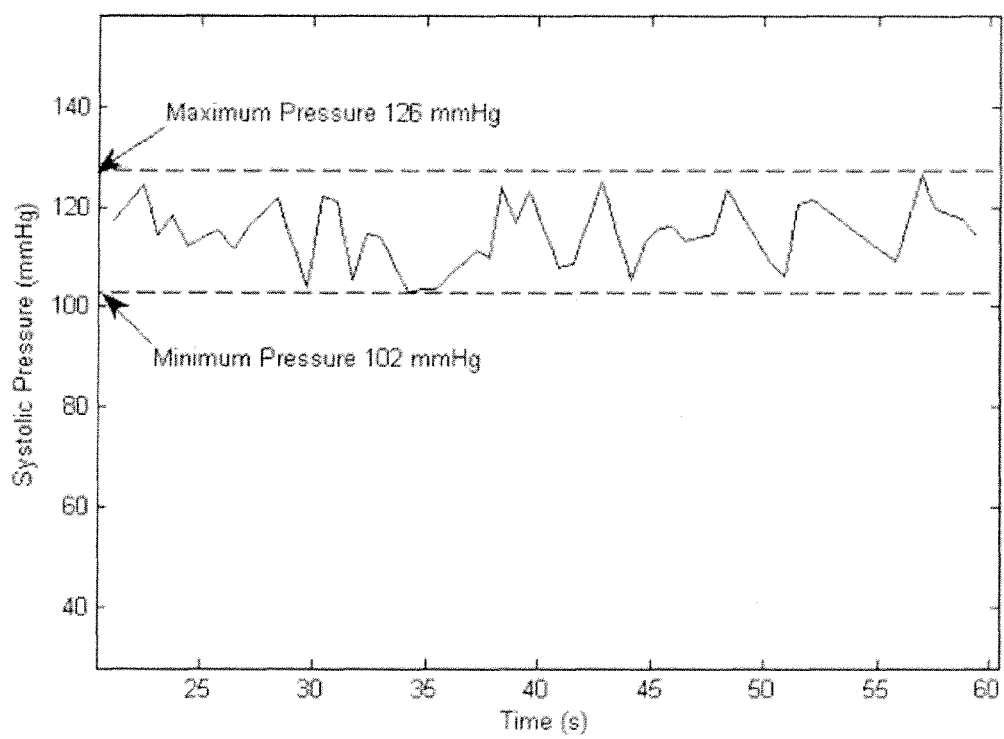
FIG. 18 shows a plot of systolic pressure values measured for a duration of 60 seconds in a single data set.

The vascular transit time (VTT) was analyzed based on the audio and video samples measured together. For every single pulse in the data set, a VTT can be derived. However, the VTT can change on every pulse since there is a continuous variation of pressure in a human throughout the day. By using the proposed method, the systolic pressure was determined with a single VTT value but the probability of erroneous results was high. Thus, for all the analyzed data sets, the median of the VTT was taken to compute the blood pressure. FIG. 18 shows a plot for systolic pressure values for a duration of 60 seconds in a single data set. The sample data set varied within a range of 24 mmHg. The median of the pressure value resulted in 113 mmHg which was exactly the same from the blood pressure meter for that instant.

The results from Table 10 below introduce the problem involved in the selection of number of data points. Table 10 shows the variation of estimated (Es) systolic pressure ($P_s$) from measured (Md) based selection of number of data points from a data set. Although the systolic pressure can be estimated by selecting a single data point, the accuracy of the values will be very low. Table 10 contains four data sets showing the pressure values with different number of data points selected. A single point was taken at random from minute a data set and compared against the actual pressure value. In a similar manner, the pressure value was computed by selecting five and ten points. All the plots showed results close to actual pressure, but the closeness increased with increase in the number of data points selected. From the Table 10, it can be inferred that the selection of at least 10 data points from the data set yielded closer values of pressure.

TABLE 10

| Sample | Md Ps | 1 point | 5 points | 10 points |
|---|---|---|---|---|
| 1 | 110 | 105 | 112 | 110 |
| 2 | 115 | 110 | 110 | 112 |
| 3 | 108 | 101 | 112 | 107 |
| 4 | 104 | 115 | 114 | 111 |

The cuff-less differential blood pressure estimation technique described herein uses mobile phone and their built-in sensors. Synchronization is followed by procedures for localizing and detecting heart beat and pulse signals. The mathematical formulations used to estimate the systolic and diastolic pressure produce accuracies between (95-100%).

Some technical and social issues arise which require consideration in the use of the present cuffless differential estimation of blood pressure. First, the method of measuring pulses with the video intensity is native without much filtering. Hence, the appearance of sharp peaks may hardly be detected. The addition of special hardware may effectively increase the accuracy and reliability of the device, but it voids the system's purpose. Also, the hardware specifications for all devices are not standard. Device incompatibilities will most likely occur. For example, the LED flash available in one phone may not be present in all devices as standard. Also, software version differences make the applications to work only on certain devices. Heart beat recording also requires placement of the microphone over the bare chest. Taking measurements with the shirts on does not give desirable results. Hence, the measurement may not be possible in public. Further, people with chronic cardiac and vascular disorder may not follow the same VTT-Systolic pressure relation. In addition, the accuracy of estimation technique was less when the tests were performed with the subject lying flat on the ground. The subject preferably needs to be sitting upright with the arm holding the camera in level to the heart. Finally, the present investigation required the use of rooted phones which are popular only among developers. API changes have to be made, to incorporate changes in these phone's system or the application should be added as a core system process to be used by all public users.

EXAMPLE 7A

Sensitivity Analysis

The cuffless estimation technique's sensitivity was determined by studying the relation between different parameters. Firstly, the relation between the cardiac output and a person's height and weight was studied. Cardiac output is defined as the volume of blood being pumped by the heart in a time interval of one minute. Mathematically, it is the product of heart rate and stroke volume which were obtained as explained above. Because cardiac output increases with an increase in an individual's body-surface area, the person's blood pressure also increases linearly. Also, the cardiac output increases more rapidly with height rather than with the weight of the individual, i.e., tall individuals have higher cardiac output than obese individuals.

The sensitivity of the recording device also must be considered while considering in the sensitivity analysis. The software cap on the Android platform for Nexus One prevents the hardware from performing to its original capability i.e. the hardware camera is reported to record video at 720 pixels at a rate of 30 fps, but the recording capability has been restricted to 24 fps at 480 pixels resolution. All the specifications discussed here are results of testing the Nexus One's camera under bright lighting conditions. When the picture gets darker, the frame rate decreases considerably. It was observed during the test setup that the average frame rate dropped from 23 fps to 17-16 fps. Every frame occurred at an average time interval of 62.5 ms. Based on this estimate, we conclude that the accuracy of ejection time varied between 0-120 ms in a data set and that the accuracy of results varied from 0-45 mmHg of mercury. Even the accuracy of pulse pressure ranged between 0-18 mmHg. For example, if a median error of +24 ms of ET is considered for the results, an actual 120/80 mmHg systolic pressure will show as 145/96. To eliminate this kind of error phenomenon, the median value of the ejection times was taken in a data set, thereby improving the current system's accuracy.

An analysis was made into whether factors such as age, height, and weight affect the system's sensitivity. The tests were performed with subjects of varying age, height, and weight as listed in Table 11 below.

TABLE 11

| Subject | Age | Height (ft) | Weight (lbs) |
|---|---|---|---|
| Data 1 | 22 | 6.0 | 149 |
| Data 2 | 28 | 6.1 | 142 |
| Data 3 | 23 | 5.8 | 140 |
| Data 4 | 25 | 5.8 | 145 |
| Data 5 | 13 | 5.5 | 123 |

Figure 19:
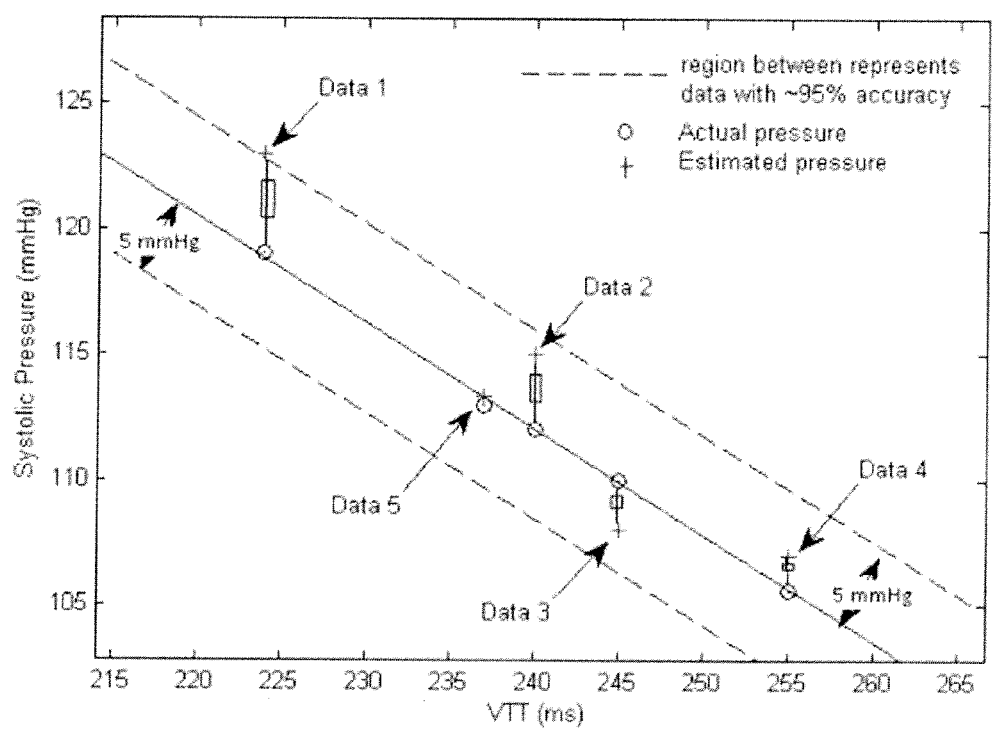
FIG. 19 shows a plot of systolic pressure versus VTT compared to data for various individuals.

By obtaining the VTT and $P_s$ for the five subjects as explained above, the estimated values of Ps from VTT were compared with the pressure measured using a meter. FIG. 19 shows a plot of Systolic pressure vs VTT. The meter based readings are joined by a straight dark line in the center. The points labeled as 'Data' refer to different individuals. The results obtained by applying Equation 6 to all the individuals regardless of the age, height or weight for $P_s$ computation, yielded accuracies of above 95%. Based on these results, it can be inferred that factors such as age, height, and weight did not impact the end result of proposed system. It was also observed that, for an increase of 10 ms of VTT, the systolic pressure dropped linearly by 4.25 mmHg. Based on the information from the sensitivity analysis, it can be concluded that the system will work under most conditions regardless of the physique of the individual. However, the method has not been tested with people having a history of cardiac disorders. The results and accuracy could also vary for people with ailments and disabilities due to changes in their vascular system.

EXAMPLE 7B

Mobile Hardware Performance Analysis

The accuracy of results depends on the performance of a system under any conditions. A performance analysis could shed further light on the modules within the system that may need improvement or adjustment for better estimation. The synchronization process and some hardware constraints are emphasized.

First, synchronization is a very important module in the proposed differential estimation of blood pressure. The proposed system uses two mobile phones in a master-slave relationship for collecting data. When the time difference between the clocks increases, the probability of selecting the correct S1 sound for the corresponding video of the systolic pulse decreases. If the clocks are working off sync, the resulting values from the estimation are incorrect.

To estimate the performance of the device, it was assumed that the one-way network delay is the same on both sides, i.e., the time taken for a message from a master to a slave is the same as the time taken for transit from a slave to the master. A small test for the effectiveness of the synchronization process was done. Because it was difficult to have a centralized time for verification of synchronization process of two mobile phones, performance was measured in an alternative method as follows.

First, the devices to be synchronized for the estimation were labeled as Device 1 and Device 2. Device 1 was made to act as the master device and synchronized making note of the offset. Device 2 was made to act as the slave device and synchronized making note of the offset. When the offset value is 0, the clocks between the devices are perfectly synchronized. Steps 2 and 3 were repeated to verify zero offset value in both directions. The performance test was conducted on two pairs of devices: Nexus One vs Nexus One and Nexus One vs HTC Hero. Hero and Nexus One do not have a common hardware configuration. Hence, there was a tradeoff in the network delay. Table 12 below shows the effectiveness of the clock after synchronizing the two Nexus One mobile phones. Based on this experiment, it was found that the lower the offset time between devices, the Greater the effectiveness. The offset varied between ±1 ms, which showed an effective synchronization of the clock times in both devices. The results for Nexus one vs Hero showed a similar behavior, but the round trip time (RTT) between the devices was 79 ms and the offset varied between ±6 ms.

TABLE 12

| Device | RTT (ms) | Offset (ms) |
|--------|----------|-------------|
| 1 | 30 | 1 |
| 2 | 29 | −1 |
| 1 | 30 | −1 |
| 2 | 29 | 0 |
| 1 | 29 | 0 |
| 2 | 29 | 0 |
| 1 | 29 | 0 |
| 2 | 29 | −1 |
| 1 | 29 | 1 |
| 2 | 29 | 0 |

Figure 20:
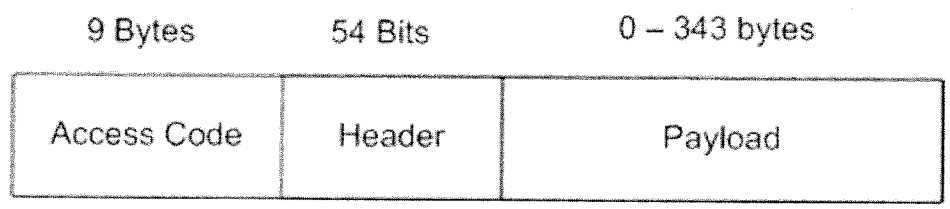
FIG. 20 shows the generalized structure of a data packet.

A Bluetooth device can transmit data at a rate of 780 kbps according to the IEEE 802.11 standards. The effective transmission and reduction of the RTT relies on the size of messages being sent and the processor capability to handle multiple requests, interference and attenuation of signal. In the present investigation, the devices were placed as close as possible to eliminate the delay introduced due to signal issues. Also the message size being transmitted was very small for a bandwidth of 780 kbps. Therefore data loss due to retransmissions or transmission delays due to buffer overflows did not occur in the system. FIG. 20 gives the generalized packet structure of a Bluetooth data packet. During the synchronization process, a timestamp value of long data type was being sent back and forth during a time instant. Considering the payload size as 128 bits, approximate size of an individual data packet was about 32 bytes. The mechanism works on simplex method sending data in one direction at a time. Hence, the message size will not create issues in transmission.

The detection of heart sounds relies on the microphone's ability to pick up low-frequency, low-amplitude audio signals. Every mobile phone in the market has different hardware specifications. Two brands of phones may not have the same kind of hardware. However, a device with the best microphone sensitivity could help in recording the heart beats accurately. Thus, a comparison of microphones on three devices was also made.

Figure 21:
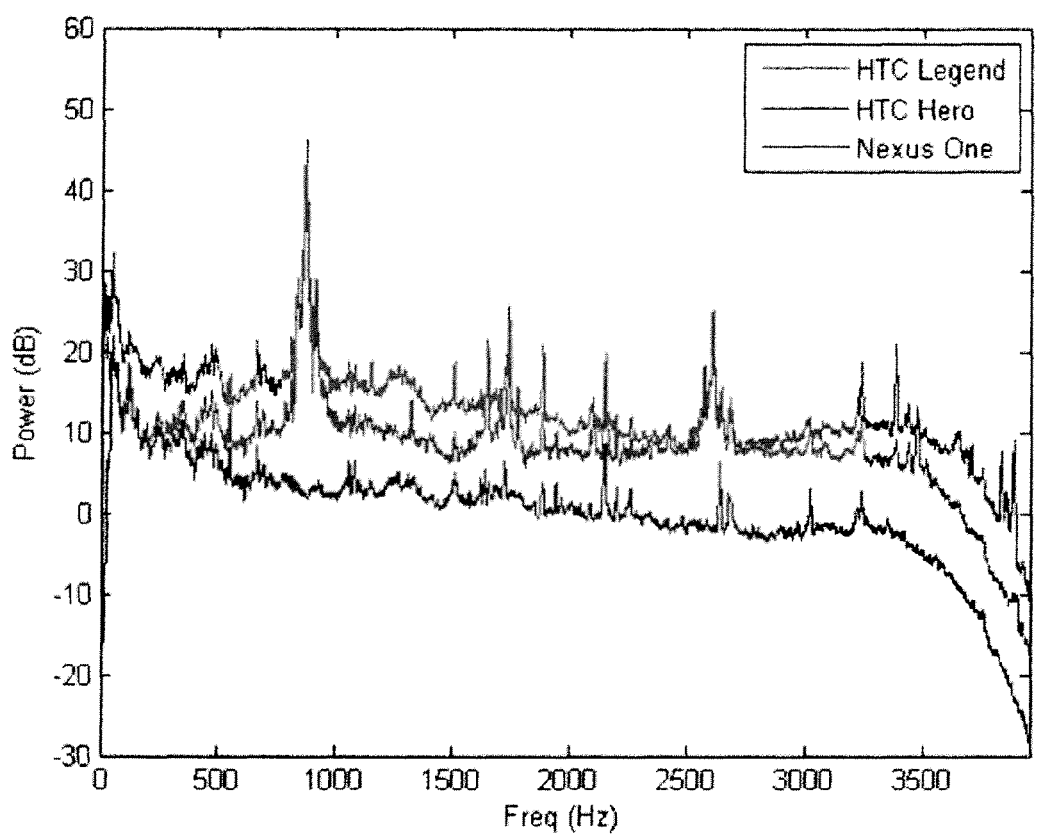
FIG. 21 shows microphone frequency response for three different mobile phones.

First, a test was performed to determine the frequency response of the microphone on three devices, namely, Google's Nexus One, HTC Hero, and HTC Legend. The test occurred in a closed environment with ambient noise and few audio activities. The three phones recorded the same audio simultaneously. The recorded audio NA as processed in MATLAB to derive a frequency response. FIG. 21 shows the microphone frequency response for three different mobile phones. FIG. 21 shows a flatter response curve for Hero than Legend and Nexus One. Legend has the highest power in the low frequency spectrum followed by Hero and Nexus One. Also, the occurrence of peaks in the audio data due to external disturbance was seen only in Hero and Legend. Where as it was eliminated in Nexus One by the hardware noise cancellation available on the phone. Thus, heart beats were more accurately detected using Legend or Hero than Nexus One.

REFERENCES

The following documents and publications are hereby incorporated by reference.

OTHER PUBLICATIONS

Song, W., et al., "Next Generation 9-1-1 Proof-of-Concept System," SIGCOMM 2008.

United Kingdom Department of Health—AMPDS Call Categorization Version 11: Her Majesty's Stationery Office, April 2005.

SAMU Online (http://www.samu-de-france.fr/en)

NENA NG911 Project Online (http://www.nena.org/ng911-project)

NENA i3 Technical Requirements Document, (http://www.nena.org/standards/technical/voip/i3-requirements)

Nada Hashmi, Dan Myung, Mark Gaynor, Steve Moulton, "A Sensor-based web service-enabled emergency medical response system", EESR '05, June 2005.

Fredrik Bergstrand, Jona Landgren, "Sharing Using Live Video in Emergency Response Work", Proceeding of the $6^{th}$ International ISCRAM Conference—Gothenburg, Sweden, May 2009.

Roman Belda, Ismael de Fez, Francisco Fraile, Vicot Murcia, Pau Arce, Juan Carlos Guerri, "Multimedia System for emergency Services over TETRA-DVBT Networks", $34^{th}$ Euromicro Conference Software Engineering and Advanced Applications, 2008.

Reinvuo T., Hannula M., Sorvoja H., Alasaarela E., Myllyla R., "Measurement of Respiratory Rate with Hih-Resolution Accelerometer and EMFit Pressure Sensor", IEEE Sensor Application Symposium, February 2006.

Rendon D. B., Rojas Ojeda J. L., Crespo Foix L. F., Morillo D. S., Fernandez M. A., "Mapping the Human Body for Vibrations using an Accelerometer", Proceeding of the $29^{th}$ Annual Conference of the IEEE EMBS. August 2007.

Su S. W., Cellar B. G., Savkin A. V., Nguyen H. T., Chena T. M., Guo Y., Wang L., "Transient and Steady State Estimation of Human Oxygen uptake based on Noninvasive Portable Sensor Measurements", Medical Biology Engineering Computation, March 2009.

Phan D. H., Bonnet S., Guillemaud R., Castelli E., Pham Thi N.Y., "Estimation of Respiratory Waveform and Heart Rate using Accelerometer", 30th Annual International IEEE EMBS Conference, August 2008

Richard Chipman. Roger Wuerfel, "Network Based Information sharing Between Emergency Operations Center", IEEE Conference on Technologies for Homeland Security 2008.

Green M. W., Sparks R., Pritchard D. A., "Real-time Video Surveillance for First Responders in an Emergency Situation", IEEE International Conference on Security Technology 2008.

Jeong O., Lee I. Shin-Gak K., "Consideration of Supporting the Multimedia Emergency Services in VOIP", International Conference on Advanced Communication Technology 2009.

Banitsas Pelegris P., Orbach T., Cavouras D., Sidiropoulos K., Kostopoulos S., "A Simple algorithm to Monitor HR for Real Time Treatment Applications", Proceedings of the 9th 2008.

J. Foo. C. Lim, and P. Wang; "Evaluation of Blood Pressure Changes Using Vascular Transit Time": Physiological Measurement, Vol 27, No, 8, 2006.

K. Banitsas, P. Pelearis, Orbach, D. Cavouras, K. Sidiropoulos, and S. Kostopoulos, "A simple algorithm to monitor hr for real time treatment applications," November 2009, pp. 1-5.

J. Y. A. Foo, C. S. Lim, and P. Wang. "Evaluation of blood pressure changes using vascular transit time," Physiological Measurement, vol. 27, no. 8, p. 685, 2006. [Online]. Available: http://stacks.iop.org/0967-3334/27/i=8/a=003

J. N. Cohn, S. Finkelstein, G. McVeigh, D. Morgan, L. LeMay, J. Robinson, and J. Mock, "Noninvasive Pulse Wave Analysis for the Early Detection of Vascular Disease." Hypertension, vol. 26, no. 3, pp. 503-508, 1995. [Online]. Available: http://hyper.ahajournals.org/cgi/content/abstract/26/3/503

J. Alfie, G. D. Waisman, C. R. Galarza, and M. I. Camera, "Contribution of Stroke Volume to the Change in Pulse Pressure Pattern With Age," Hypertension, vol. 34, no. 4, pp. 808-812, 1999. [Online]. Available: http://hyper.ahajournals.org/cgi/content/abstract/34/4/808

What is claimed is:

1. A method for transmitting heart rate information of a subject to an emergency dispatcher, comprising:
   placing a Voice over IP ("VOIP") call to an emergency dispatcher using a mobile phone, wherein the mobile phone comprises an embedded camera with a lens, a flash, a WiFi receiver, a WiFi transmitter, VOIP software, wherein the VOIP software comprises modified signaling protocols which facilitate transmission of heart rate information in real-time, and an application for estimating heart rate information using the camera and flash, and wherein all subsequent steps are performed during the VOIP call;
   activating the application for estimating heart rate information;
   placing the finger tip of the subject on the lens of the camera;
   activating the flash of the camera to permit the application to capture a video containing information about the heart rate of the subject relating to variations in reflective index of light directed at the finger tip of the subject;
   using the application to analyze the video and estimate heart rate information of the subject, wherein the application utilizes Photo Plethysmography ("PPG"), wherein a low reflective index is represents a systolic phase and a high reflective index represents a diastolic phase, and wherein the step of using the application to analyze the video and estimate heart rate information of the subject comprises the steps of:
      dividing frames of the video into multiple regions,
      splitting pixels of a region of the frames into red, blue, and green components;
      mapping intensity of the red component of the region over an interval of time Wt to determine a number of peaks n; and
      estimating heart rate information of the subject using an equation; and
   using the modified signaling protocols of the mobile phone to transmit the heart rate information of the subject to the emergency dispatcher via an Internet-based network in real-time during the VOIP call.

2. The method of claim 1, wherein the activating the flash of the camera step occurs more than once.

3. The method of claim 1, wherein the frames of the video are divided into multiple quadrants and pixels of a quadrant are split into red, blue, and green components.

4. The method of claim 1, wherein the equation is:

$$\text{heart rate} = (n*60)/Wt.$$

5. A method for allowing an emergency dispatcher to monitor CPR chest compression rate and displacement being administered on a subject, comprising:
   placing a Voice over IP ("VOIP") call to an emergency dispatcher using a mobile phone, wherein the mobile phone comprises an embedded accelerometer, a WiFi receiver, a WiFi transmitter, VOIP software, wherein the VOIP software comprises modified signaling protocols which facilitate transmission of chest compression rate and displacement information in real-time, and an application for estimating chest compression rate and displacement information using the embedded accelerometer, and wherein all subsequent steps are performed during the VOIP call;
   activating the application for estimating chest compression rate and displacement information;
   administering chest compressions to the subject;
   activating the embedded accelerometer to permit the application to capture information about the chest compression rate and chest displacement relating to movement of the chest of the subject and calculate the chest compression rate and chest displacement of the subject, wherein the chest displacement of the subject is calculated by finding a velocity and calculating the chest displacement using an equation based on the velocity;
   using the modified signaling protocols of the mobile phone to transmit the chest compression rate and chest displacement of the subject to the emergency dispatcher via an Internet-based network in real-time during the VOIP call; and
   receiving instructions on efficient administration of chest compressions to meet acceptable CPR guidelines, wherein the acceptable CPR guidelines include a preferable depth of compressions of about 2 to about 2.5 inches and a preferable rate of about 100 to about 120 compressions per minute.

6. The method of claim 5, wherein the instructions on efficient administration of chest compressions to meet acceptable CPR guidelines are received from the emergency dispatcher and further comprising the step of administering modified chest compressions to the subject that take into account the instructions received from the emergency dispatcher.

7. The method of claim 5, wherein the chest displacement of the subject is calculated using the steps of:

finding a velocity of the mobile phone using the equation:

$$V_t = V_0 + V_d,$$

wherein $V_0$ is a starting velocity, $V_d$ is a change in velocity over a period of time, $V_t$ is a velocity after the period of time, and t is the period of time, and calculating the chest displacement using the equation:

$$\text{chest displacement} = (V_0 + V_t)/2 * t.$$

8. A method for transmitting overall health information of a subject to an emergency dispatcher, comprising:

placing a Voice over IP ("VOIP") call to an emergency dispatcher using a mobile phone, wherein the mobile phone comprises a camera with a lens, a flash, a WiFi receiver, a WiFi transmitter, VOIP software, wherein the VOIP software comprises modified signaling protocols which facilitate transmission of heart rate information and respiratory rate information in real-time, an application for estimating heart rate information using the camera and flash, an embedded accelerometer, and an application for estimating respiratory rate information using the accelerometer, and wherein all subsequent steps are performed during the VOIP call;

activating the application for estimating heart rate information;

placing the finger tip of the subject on the lens of the camera;

activating the flash of the camera to permit the application to capture a video containing information about the heart rate of the subject relating to variations in reflective index of light directed at the finger tip of the subject;

using the application to analyze the video and estimate heart rate information of the subject, wherein the application utilizes Photo Plethysmography ("PPG"), wherein a low reflective index is represents a systolic phase and a high reflective index represents a diastolic phase, and wherein the step of using the application to analyze the video and estimate heart rate information of the subject comprises the steps of:

dividing frames of the video into multiple regions, splitting pixels of a region of the frames into red, blue, and green components;

mapping intensity of the red component of the region over an interval of time Wt to determine a number of peaks n; and estimating heart rate information of the subject using an equation;

using the modified signaling protocols of the mobile phone to transmit the heart rate information of the subject to the emergency dispatcher via an Internet-based network in real-time during the VOIP call;

activating the application for estimating respiratory rate information;

placing the mobile phone on the chest of the subject;

activating the embedded accelerometer to permit the application to capture information about the respiratory rate of the subject relating to movement of the chest of the subject and calculate the respiratory rate of the subject; and using the modified signaling protocols of the mobile phone to transmit the respiratory rate of the subject to the emergency dispatcher via an Internet-based network in real-time during the VOIP call.

9. The method of claim 8, wherein the activating the flash of the camera step occurs more than once.

10. The method of claim 8, wherein the mobile phone is placed in a horizontal position on the chest of the subject to capture movement of the chest of the subject.

11. The method of claim 8, wherein irregular chest movements of the subject are captured and transmitted to the emergency dispatcher as respiratory rate information showing breathing irregularities or breathing difficulties.

12. The method of claim 8, further comprising placing the mobile phone in close proximity to the nose or mouth of the subject and transmitting breathing sounds of the subject to the emergency dispatcher.

13. The method of claim 8, wherein the camera of the mobile phone is capable of capturing still or video images and further comprising using the camera of the mobile phone to transmit still or video images of the subject to the emergency dispatcher.

14. The method of claim 13, wherein the camera transmits video images of the subject and the video images comprise information on bit rate changes, and wherein the information on bit rate changes communicates information to the emergency dispatcher regarding activity of the subject.

15. The method of claim 13, wherein all operations of the camera of the mobile phone are capable of being controlled remotely by the emergency dispatcher.

16. The method of claim 8, wherein the equation is:

$$\text{heart rate} = (n * 60)/Wt.$$

* * * * *